United States Patent
Paiam et al.

(10) Patent No.: US 12,194,277 B2
(45) Date of Patent: Jan. 14, 2025

(54) FAST OCCLUSION DETECTION IN INFUSION DEVICES

(71) Applicant: CareFusion 303, Inc., San Diego, CA (US)

(72) Inventors: Reza Paiam, San Diego, CA (US); Michael K. Workman, Carlsbad, CA (US)

(73) Assignee: CareFusion 303, Inc., San Diego, CA (US)

( * ) Notice: Subject to any disclaimer, the term of this patent is extended or adjusted under 35 U.S.C. 154(b) by 544 days.

(21) Appl. No.: 17/240,857

(22) Filed: Apr. 26, 2021

(65) Prior Publication Data

US 2021/0330881 A1    Oct. 28, 2021

Related U.S. Application Data

(60) Provisional application No. 63/016,918, filed on Apr. 28, 2020.

(51) Int. Cl.
*A61M 5/168* (2006.01)
*G06N 20/00* (2019.01)
*A61M 5/142* (2006.01)

(52) U.S. Cl.
CPC .... *A61M 5/16831* (2013.01); *A61M 5/16886* (2013.01); *G06N 20/00* (2019.01);
(Continued)

(58) Field of Classification Search
CPC ........ A61M 2205/583; A61M 2205/18; A61M 2005/16872; A61M 2005/16868;
(Continued)

(56) References Cited

U.S. PATENT DOCUMENTS 9,833,561 B2   12/2017  Chambers et al.
10,265,463 B2*  4/2019  Biasi ...................... F04B 53/08
(Continued)

FOREIGN PATENT DOCUMENTS

WO    WO-9804303         2/1998
WO    WO-2013176770 A2   11/2013

OTHER PUBLICATIONS

International Search Report and Written Opinion for Application No. PCT/US2021/029221, dated Aug. 13, 2021, 21 pages.
(Continued)

*Primary Examiner* — Aditya S Bhat
(74) *Attorney, Agent, or Firm* — Morgan, Lewis & Bockius LLP

(57) ABSTRACT

A method for detecting an occlusion in a fluidic channel of an infusion device that includes flowing a fluid within the fluidic channel during a first period of time in which a flow rate of the fluid is set to a first flow rate; pausing, the flow rate for a second period of time; measuring, a first pressure at a location along the fluidic channel during the second period of time; increasing, after measuring the first pressure, the flow rate to a second flow rate; pausing, the flow rate for a fourth period of time; measuring, after pausing the flow rate, a second pressure at the location during the fourth period of time; computing, at a processor, a difference between the first and second pressures; and in accordance with a determination that the magnitude of the difference satisfies the threshold, providing an indication, of a presence of the occlusion.

20 Claims, 18 Drawing Sheets

(52) U.S. Cl.
CPC ............. *A61M 2005/14208* (2013.01); *A61M 2005/16868* (2013.01); *A61M 2005/16872* (2013.01); *A61M 2205/18* (2013.01); *A61M 2205/583* (2013.01)

(58) Field of Classification Search
CPC .... A61M 2005/14208; A61M 5/16886; A61M 5/16831; G06N 20/00
USPC .......................................................... 702/45
See application file for complete search history.

(56) References Cited

U.S. PATENT DOCUMENTS

| | | | |
|---|---|---|---|
| 2017/0266378 A1* | 9/2017 | Kamen | A61M 5/16827 |
| 2019/0117891 A1 | 4/2019 | Carothers et al. | |
| 2019/0316948 A1* | 10/2019 | Karol | A61M 1/159 |

OTHER PUBLICATIONS

Written Opinion from the International Preliminary Examining Authority for Application No. PCT/US2021/029221, dated Mar. 29, 2022, 12 pages.

International Preliminary Report on Patentability from the International Preliminary Examining Authority for Application No. PCT/US2021/029221, dated Jul. 21, 2022, 29 pages.

* cited by examiner

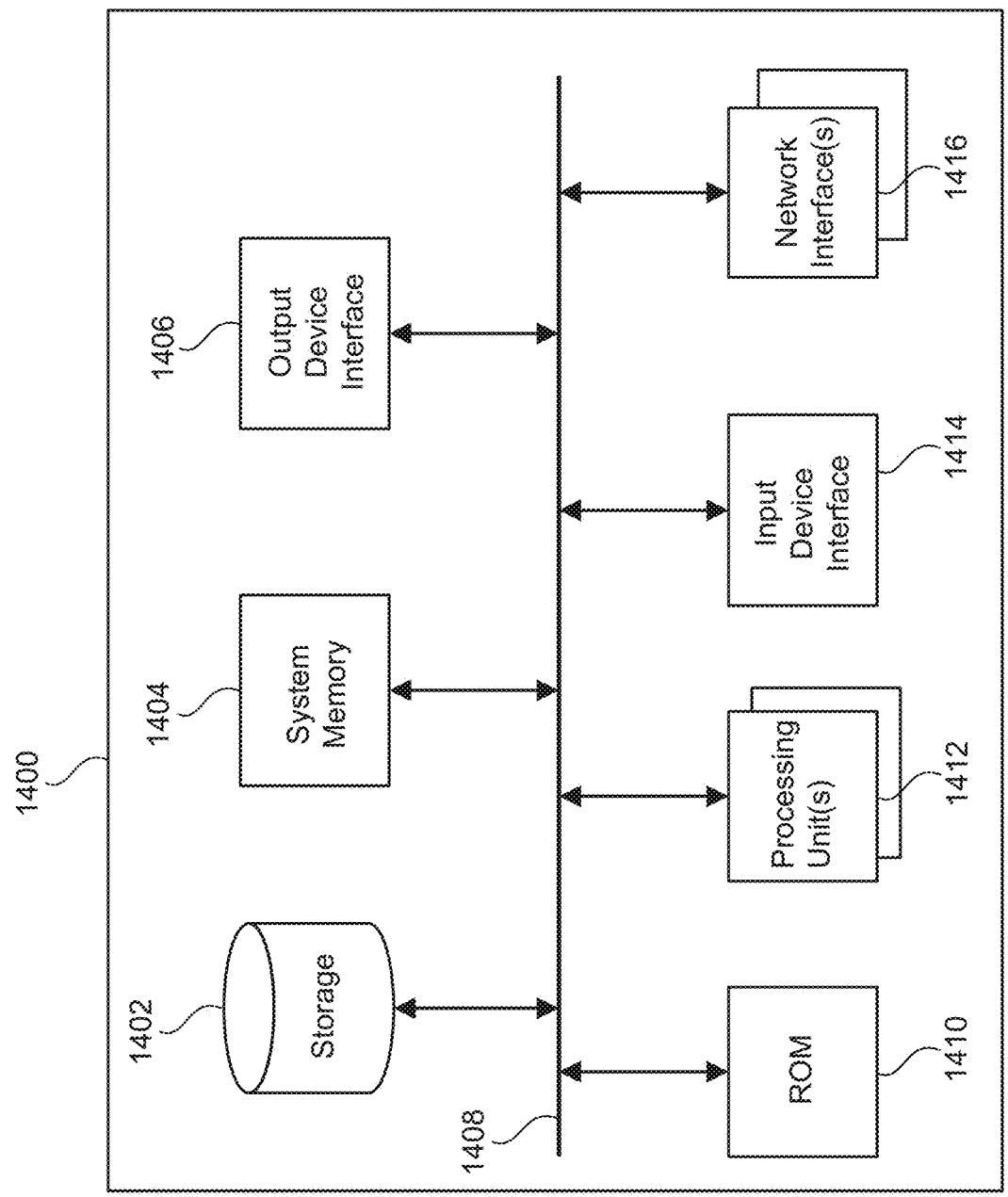

FAST OCCLUSION DETECTION IN INFUSION DEVICES

RELATED APPLICATIONS

This application claims priority to U.S. Provisional Application Ser. No. 63/016,918, filed Apr. 28, 2020, which is incorporated by reference herein in its entirety.

TECHNICAL FIELD

This application relates generally to detecting occlusions in infusion devices.

BACKGROUND

Medical devices such as infusion devices are used to infuse medical fluids to patients. During operation of an infusion device, an occlusion (e.g., a blockage) can form within an infusion path along which a medical fluid is infused to a patient (e.g. within an intravenous line), interrupting the infusion of the medical fluid to the patient.

There is a need for faster detections of occlusions in infusion devices to, for example, conserve device resources and minimize possible harm to the patient.

SUMMARY

An occlusion condition in an infusion line (e.g., in an intravenous line) could result in patient harm due to an interruption in a therapy, and in an infusion of an inadvertent bolus volume to the patient after the occlusion is released. It is desirable to detect the occlusion condition as early as possible to reduce the size of this inadvertent and potentially harmful bolus. The sooner an occlusion condition is detected, the smaller the amount of the bolus volume infused to the patient after an occlusion release. Similarly, early detection of an occlusion reduces the harmful effects of an infusion interruption to the patient. Furthermore, early detection of an occlusion can reduce strain on the pump thereby conserving the resources needed to deliver the fluid such as power, pumping motor cycles, and pumping finger wear. Still further, the early detection can reduce strain on the set (e.g., tubing) used to deliver the fluid by quickly identifying pressure events and taking corrective action to prevent further pressure increase, and, in some instances, reduce the pressure in the set. Accordingly, there is a need for methods and systems that can detect occlusions faster to reduce harmful effects of occlusions.

Time to Alarm (TTA) describes the time between an onset of an occlusion (upstream and/or downstream) in the infusion path to the infusion device sounding an alarm to alert a clinician or a patient of the occlusion. Tables 1-3 show typical values of TTA and sizes of bolus after an occlusion release for a large volume pump (LVP) and a syringe pump. TTA values of up to several hours are possible in both LVP and syringe pumps. Inadvertent bolus volumes of up to 1 ml in syringe pump and up to 0.6 ml in LVP are possible.

TABLE 1

TTA in a LVP for downstream and upstream occlusions.

| Downstream or Upstream | Pressure Limit (mmHg) | Flow rate (ml/h) | Time To Alarm |
|---|---|---|---|
| Downstream Occlusion | 525 | 0.1 | 7.5 hours |
| | 525 | 1 | 45 minutes |
| | 525 | 25 | 2 minutes |
| | 50 | 1 | 5 minutes |
| | 50 | 0.1 | 50 minutes |
| Upstream Occlusion | | 1 | 30 minutes |
| | | 0.1 | 4 hours |

TABLE 2

TTA for a syringe pump with and without a pressure disc.

| Pressure Limit | Flow rate (ml/h) | Time To Alarm with no pressure Disc | Time To Alarm with pressure Disc |
|---|---|---|---|
| High (No Pressure Disc) 1000 mmHg (with Pressure Disc) | 0.1 | 30 hours | 24 hours |
| | 1 | 120 minutes | 105 minutes |
| | 5 | 30 minutes | 30 minutes |
| Low (No Pressure Disc) 25 mmHg (with Pressure Disc) | 0.1 | 11 hours and 30 minutes | 4 hours and 7 minutes |
| | 1 | 50 minutes | 17 minutes |
| | 5 | 23 minutes | 9 minutes |

TABLE 3

Volume of inadvertent bolus released after a release of an occlusion in a LVP Pump and a syringe pump.

| LVP or Syringe | Pressure Limit (mmHg) | Inadvertent Bolus (ml) |
|---|---|---|
| Syringe pump with no Pressure Disc | 200 (Low) | 0.51 |
| | 500 (Medium) | 0.78 |
| | 800 (High) | 1.1 |
| Syringe pump with Pressure Disc (with Back off disabled) | 300 | 0.46 |
| | 500 | 0.58 |
| | 1000 | 0.84 |
| LVP | 525 | 0.6 |
| | 50 | 0.3 |

The methods and systems described here allow occlusion conditions in infusion pumps to be detected much more quickly. The methods and systems are applicable to all infusion pumps including Large Volume Pumps (LVPs) and syringe pumps. For example, the methods are capable of detecting both downstream and upstream occlusion conditions in LVP pumps, including LVP pumps of different technologies such as peristaltic pumps, piston pumps, and diaphragm pumps, etc. Thus, the methods are not limited to infusion pumps of any specific technology. Methods described here exploit the differences in measured dynamic forces (or pressures) when an infusion pump is under an occlusion condition compared with an infusion pump operating under a normal infusion condition when no occlusion exists. Using a specific diagnostic (e.g., probing) flow rate profile, the methods generate a measurable pressure signature that differentiates an occlusion condition from a normal infusion condition.

The methods and systems disclosed herein allow an occlusion condition in an infusing device to be detected much earlier. The methods are particularly helpful at low flow rates to shorten (e.g., significantly shorten) TTAs compared to conventional systems. Even though the description below focuses on detection of downstream occlusion conditions, the methods are equally applicable for upstream occlusion detection.

The disclosed subject matter relates to a method for detecting an occlusion in a fluidic channel in an infusion device. In accordance with some implementations, the method includes computing, at a processor, a difference between a first pressure at a location along the fluidic channel during a first time interval and a second pressure at the location during a second time interval later than the first time interval. The method includes determining if a magnitude of the difference satisfies a threshold and in accordance with a determination that the magnitude of the difference satisfies the threshold: providing an indication at an output of the infusion device of a presence of the occlusion. The first time interval is separated from the second time interval by a third interval. A first flow rate during the first time interval and a second flow rate during the second time interval are both lower than a third flow rate during the third time interval.

The disclosed subject matter also relates to a machine-readable medium embodying instructions that, when executed by a machine, allow the machine to perform a method for detecting an occlusion as described herein.

The disclosed subject matter also relates to a system for detecting an occlusion. The system includes one or more processors and a memory including instructions that, when executed by the one or more processors, cause the one or more processors to perform the steps of the method described herein.

The subject technology provides a system for detecting an occlusion, including one or more processors and a memory. The memory includes instructions that, when executed by the one or more processors, cause the one or more processors to compute a difference between a first pressure at a location along a fluidic channel during a first time interval and a second pressure at the location during a second time interval later than the first time interval; determine if a magnitude of the difference satisfies a threshold; and in accordance with a determination that the magnitude of the difference satisfies the threshold: provide an indication of a presence of an occlusion along the fluidic channel. The first time interval is separated from the second time interval by a third interval, a first flow rate during the first time interval and a second flow rate during the second time interval are both lower than a third flow rate during the third time interval. Other aspects include corresponding methods, apparatus, and computer program products for implementation of the corresponding system and its features.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

FIG. 14 is a conceptual diagram illustrating an example electronic system for automatically adapting control of a medical device responsive to detecting a hostile environment, according to aspects of the subject technology.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Figure 1A:
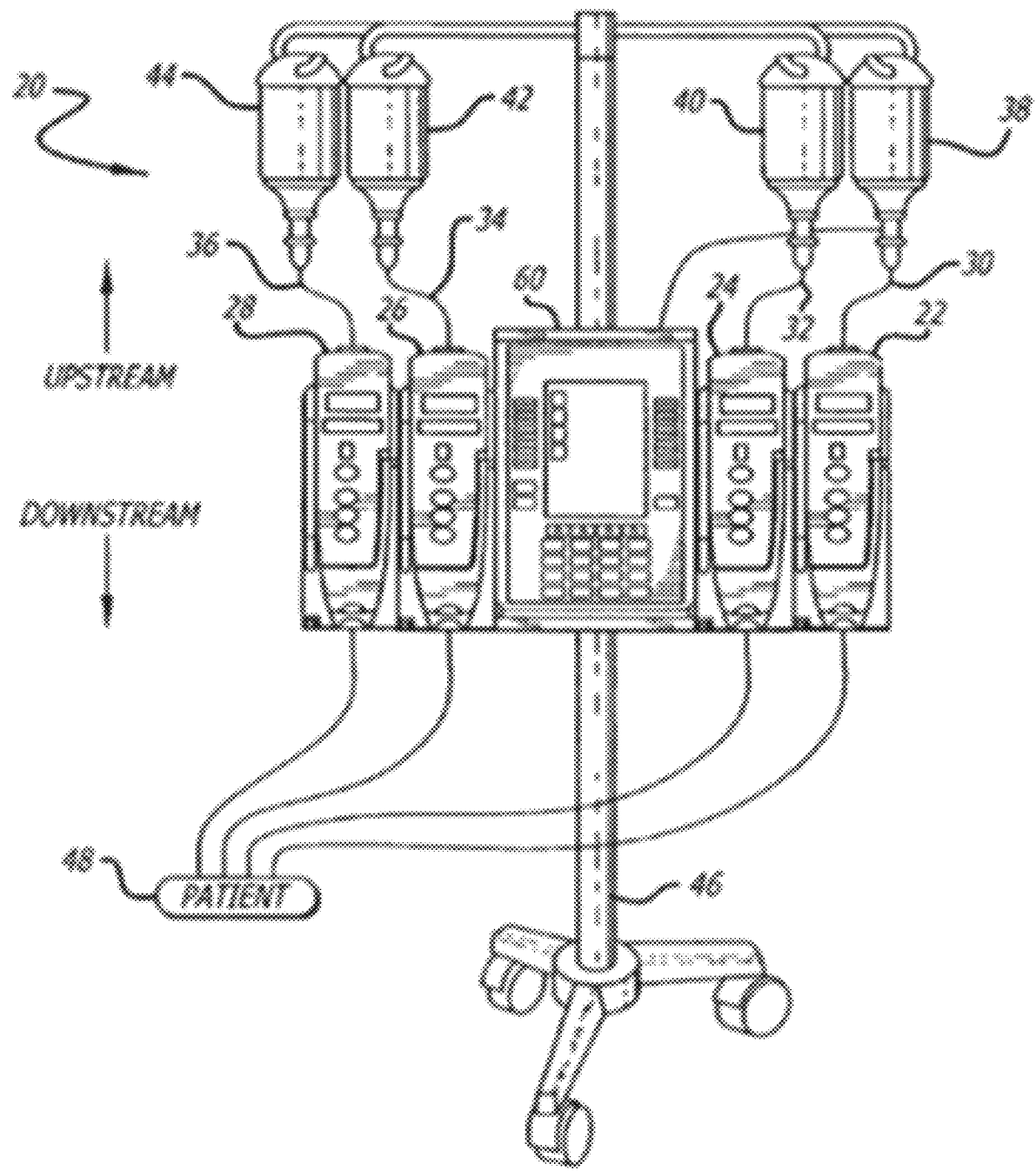
FIG. 1A is an example patient care system that includes an infusion device.

FIG. 1A is an example patient care system, according to various aspects of the subject technology. The patient care system 20 shown in FIG. 1A includes four fluid infusion pumps 22, 24, 26, and 28 each of which is in operative engagement with a respective fluid administration set 30, 32, 34, and 36. Fluid supplies 38, 40, 42, and 44, which may take various forms but in this case are shown as bottles, are inverted and suspended above the pumps. Fluid supplies may also take the form of bags or other types of containers. Both the patient care system 20 and the fluid supplies 38, 40, 42, and 44 are mounted to a roller stand or pole 46. The specific fluid supplies as well as their orientation (e.g., mount location, mount height, mounting type, etc.) within the care area may generate one or more interaction records. The interaction record for a set for example may be generated in part by detecting a scannable code associated with the set or detecting a physical structure on the set that encodes identifying information for the set prior to use.

As shown in the example implementation of FIG. 1A, each administration set 30, 32, 34, and 36 is connected between a respective fluid supply 38, 40, 42, and 44 and the same patient 48 so that the patient may receive the fluids in all the fluid supplies. The administration set may be identified either actively by, for example, scanning by a clinician or passively by, for example, wireless or optical detection of the administration set.

A separate infusion pump 22, 24, 26, and 28 is used to infuse each of the fluids of the fluid supplies into the patient. The infusion pumps are flow control devices that will act on the respective tube or fluid conduit of the fluid administration set to move the fluid from the fluid supply through the conduit to the patient 48. Because individual pumps are used, each can be individually set to the pumping or operating parameters required for infusing the particular medical fluid from the respective fluid supply into the patient at the particular rate prescribed for that fluid by the clinician.

Typically, medical fluid administration sets have more parts than are shown in FIG. 1. Many have check valves, drip chambers, valved ports, connectors, and other devices well known to those skilled in the art. These other devices have not been included in the drawings so as to preserve clarity of illustration.

Figure 1B:
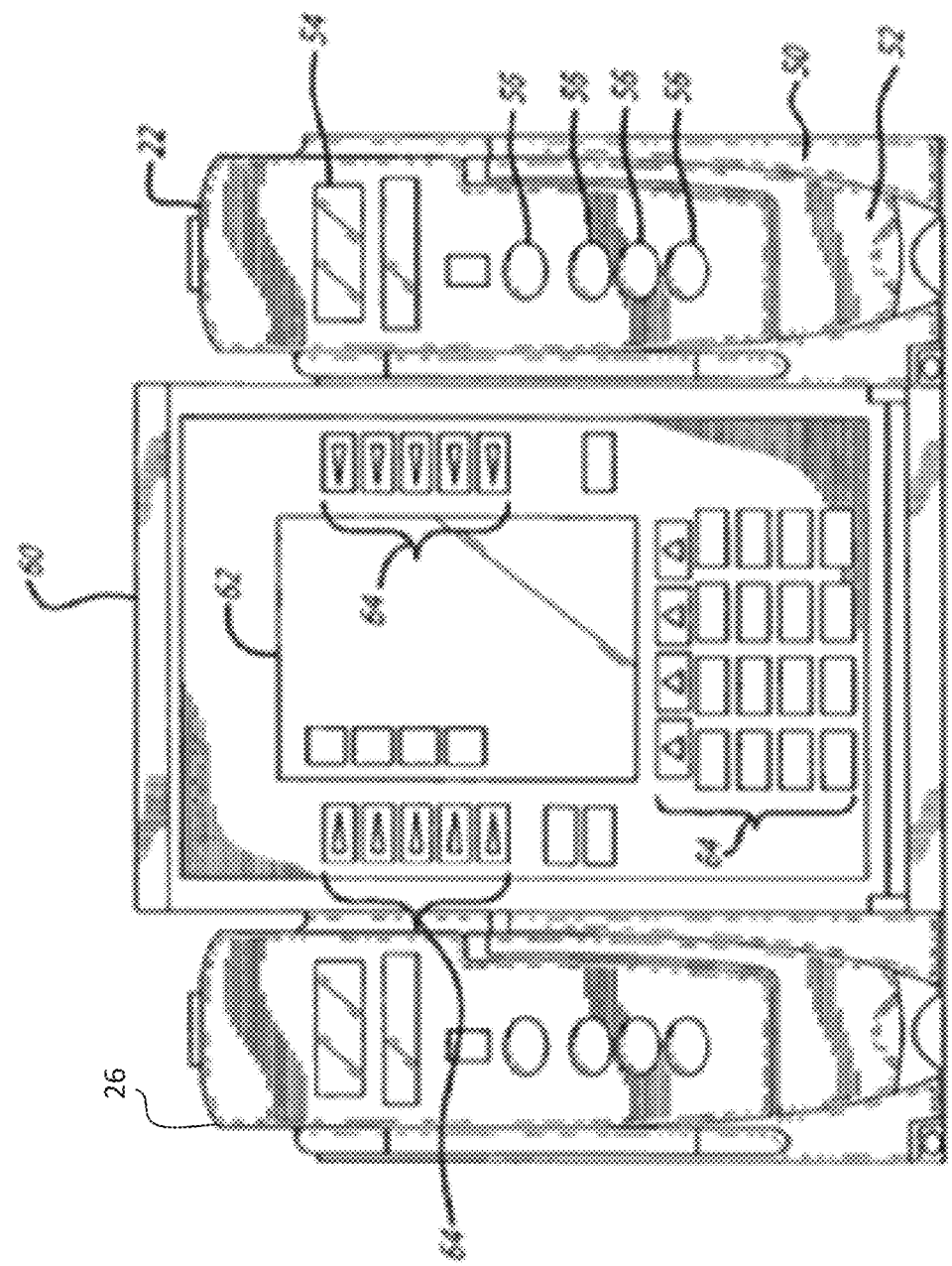
FIG. 1B is a closer view of a portion of the patient care system shown in FIG. 1A.

FIG. 1B is a closer view of a portion of the example patient care system shown in FIG. 1A, according to various aspects of the subject technology. FIG. 1B shows two of the fluid infusion pumps mounted at either side of a programming module, and the displays and control keys of each, with the programming module being capable of programming both infusion pumps. The pump 22 includes a door 50 and a handle 52 that operates to lock the door in a closed position for operation and to unlock and open the door for access to the internal pumping and sensing mechanisms and to load administration sets for the pump. When the door 50 is open, the tube can be connected with the pump 22. When the door 50 is closed, the tube is brought into operating engagement with the pumping mechanism, the upstream and downstream pressure sensors, and the other equipment of the pump. A display 54, such as an LED display, is located in plain view on the door in this implementation and may be used to visually communicate various information relevant to the pump 22, such as alert indications (e.g., alarm messages). Control keys 56 exist for programming and controlling operations of the infusion pump as desired. In some implementations, the control keys may be omitted and be presented as interactive elements on the display 54 (e.g., touchscreen display). The infusion pump 24 also includes audio alarm equipment in the form of a speaker (not shown).

In the implementation shown in FIG. 1A, a programming module 60 is attached to the left side of the infusion pump 24. Other devices or modules, including another infusion pump, may be attached to the right side of the infusion pump 24 or to the left of the programming module 60, as shown in FIG. 1A. In such a system, each attached pump represents a pump channel of the overall patient care system 20. In one implementation, the programming module is used to provide an interface between the infusion pump 24 and external devices as well as to provide most of the operator interface for the infusion pump 24. Attention is directed to U.S. Pat. No. 5,713,856 entitled "Modular Patient Care System" to Eggers et al. incorporated herein by reference in which the programming module is described as an advanced interface unit.

Returning to FIG. 1B, the programming module 60 includes a display 62 for visually communicating various information, such as the operating parameters of the pump 24 and alert indications and alarm messages. The programming module 60 may also include a speaker to provide audible alarms. In some implementations, the display 62 may be implemented as a touchscreen display. In such implementations, the control keys 64 may be omitted or reduced in number by providing corresponding interactive elements via a graphical user interface presented via the display 62. The programming module 60 may include a communications system (not shown) with which the programming module 60 may communicate with external equipment such as a medical facility server or other computer and with a portable processor, such as a handheld communication device or a laptop-type of computer, or other information device that a clinician may have to transfer information as well as to download drug libraries to a programming module 60 or pump. The communication module may be used to transfer access and interaction information for clinicians encountering the programming module or device coupled therewith (e.g., pump 22 or bar code scanner). The communications system may include one or more of a radio frequency (RF) system, an optical system such as infrared, a BLUETOOTH™ system, or other wired or wireless system. The bar code scanner and communications system may alternatively be included integrally with the infusion pump 24, such as in cases where a programming module is not used, or in addition to one with the programming module 60. Further, information input devices need not be hard-wired to medical instruments, information may be transferred through a wireless connection as well.

Figure 2:
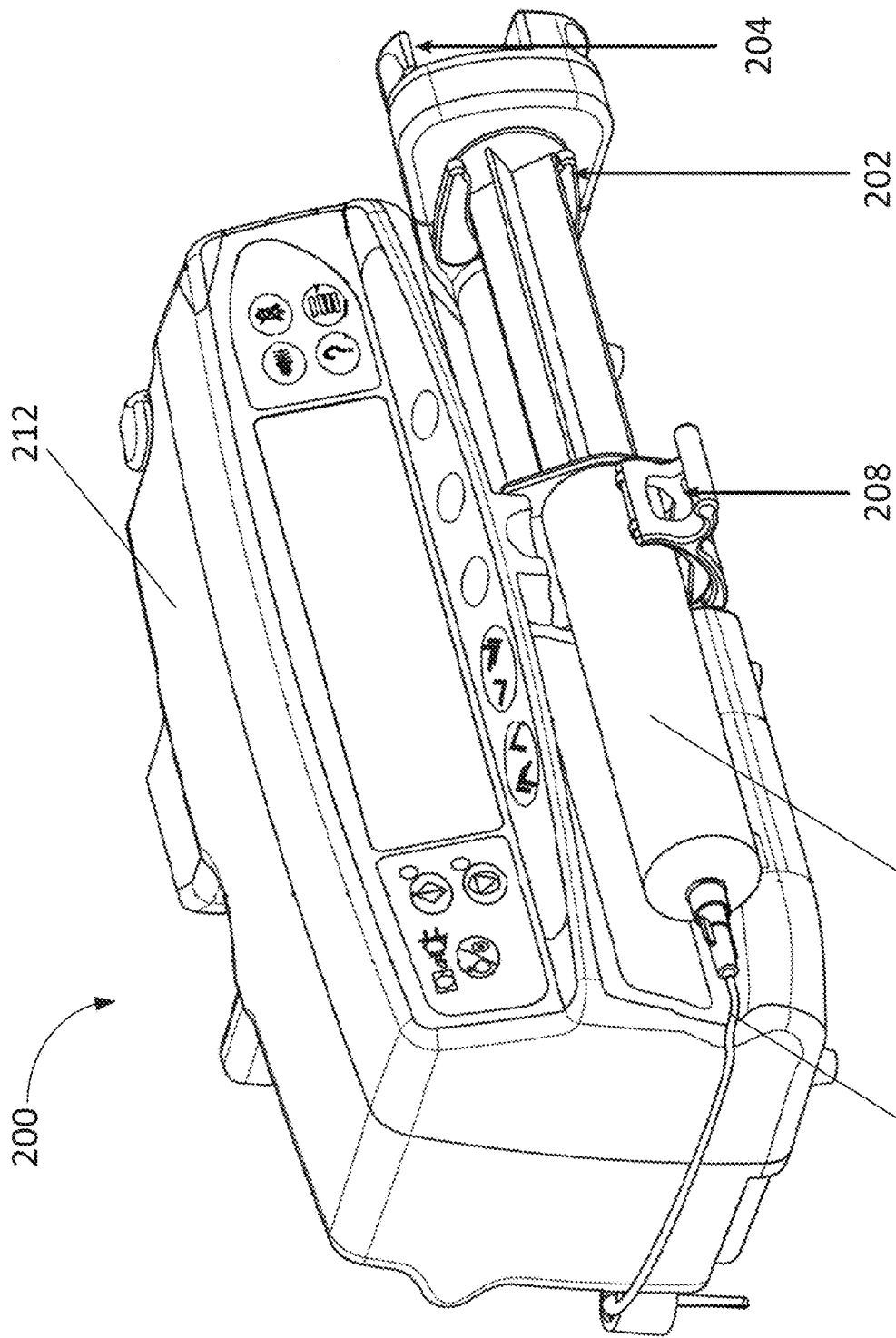
FIG. 2 is an example syringe infusion pump for which an occlusion condition can be detected according to aspects of the subject technology.

The implementation shown in FIG. 1B includes a second pump module 26 connected to the programming module 60. As shown in FIG. 1A, more pump modules may be connected. Additionally, other types of modules may be connected to the pump modules or to the programming module such as syringe pump module, as shown in FIG. 2, patient controlled analgesic module, End Tidal $CO_2$ monitoring module, oximeter monitoring module, or the like.

In some implementations, the pressure measurements from the upstream and/or downstream pressure sensors are transmitted to a server or other coordination device, and the methods disclosed herein are implemented on the server or other coordination device. For example, more sophisticated and computationally intensive approaches like machine-learning can be implemented on the server (or on a PCU with a larger memory and/or CPU resources). In some implementations, machine learning is used to identify occlusion in pressure signals received from the pump.

Figure 1C:
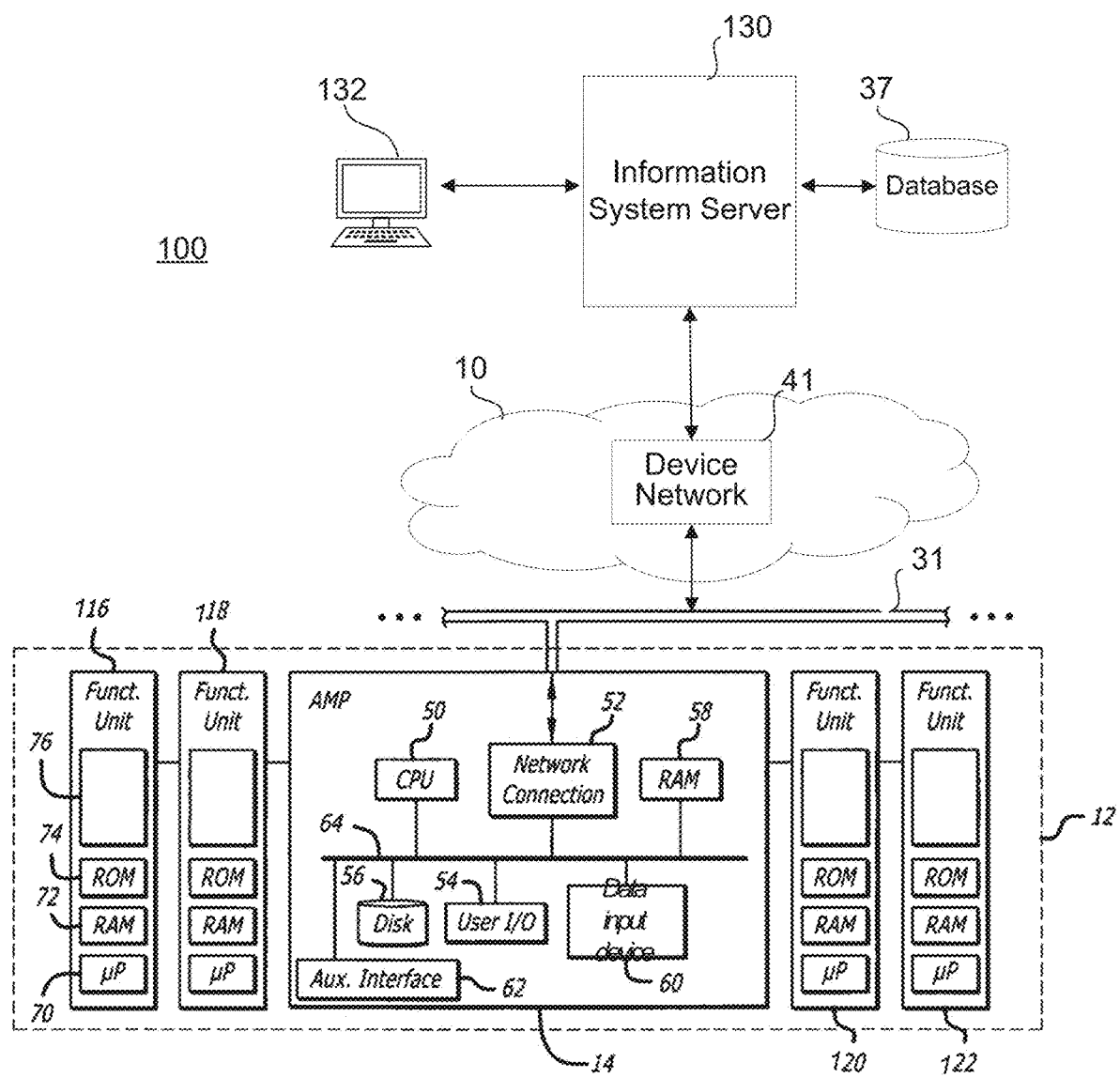
FIG. 1C depicts an example of an institutional patient care system of a healthcare organization, according to aspects of the subject technology.

FIG. 1C depicts an example of an institutional patient care system 100 of a healthcare organization, according to aspects of the subject technology. In FIG. 1C, a patient care device (or "medical device" generally) 12 is connected to a hospital network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1C optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 41 by which patient care devices 12 (and other devices) communicate in accordance with normal operations.

Additionally, institutional patient care system 100 may incorporate a separate information system server 130, the function of which will be described in more detail below. Moreover, although the information system server 130 is shown as a separate server, the functions and programming of the information system server 130 may be incorporated into another computer, if such is desired by engineers designing the institution's information system. Institutional patient care system 100 may further include one or multiple device terminals 132 for connecting and communicating with information system server 130. Device terminals 132 may include personal computers, personal data assistances, mobile devices such as laptops, tablet computers, augmented reality devices, or smartphones, configured with software for communications with information system server 130 via network 10.

Patient care device 12 comprises a system for providing patient care, such as that described in Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 116, 118, 120, 122. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1C to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 116, 118, 120 and 122, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 116, 118, 120, 122 are any devices for providing care to a patient or for monitoring patient condition. As shown in FIG. 1C, at least one of functional modules 116, 118, 120, 122 may be an infusion pump module such as an intravenous infusion pump for delivering medication or other fluid to a patient. For the purposes of this discussion, functional module 116 is an infusion pump module. Each of functional modules 118, 120, 122 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor, an intracranial pressure monitor, or the like. Functional module 118, 120 and/or 122 may be a printer, scanner, bar code reader, near-field communication reader, RFID reader, or any other peripheral input, output or input/output device.

Each functional module 116, 118, 120, 122 communicates directly or indirectly with interface unit 14, with interface unit 14 providing overall monitoring and control of device 12. Functional modules 116, 118, 120, 122 may be connected physically and electronically in serial fashion to one or both ends of interface unit 14 as shown in FIG. 1C, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 116, 118, 120, 122 may include module-specific components 76, a microprocessor 70, a volatile memory 72 and a nonvolatile memory 74 for storing information. It should be noted that while four functional modules are shown in FIG. 1C, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 116.

While each functional module may be capable of a least some level of independent operation, interface unit 14 monitors and controls overall operation of device 12. For example, as will be described in more detail below, interface unit 14 provides programming instructions to the functional modules 116, 118, 120, 122 and monitors the status of each module.

Patient care device 12 is capable of operating in several different modes, or personalities, with each personality defined by a configuration database. The configuration database may be a database 56 internal to patient care device, or an external database 37. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1C), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in health information system (HIS) server 30, decision support 48, remote data server 49, hospital department or unit stations 46, or within patient care device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

FIG. 2 shows an example syringe pump 200 infusion device, according to various aspects of the subject technology. The syringe pump 200 has a drive head that includes a plunger gripper 202 and finger grip release 204. When pressed, the finger grip release 204 causes the fingers of the plunger gripper 202 to separate to accommodate a syringe plunger. A syringe 206 holds a medical fluid to be infused by the syringe pump 200. The syringe 206 is secured by a syringe clamp 208. To deliver the medical fluid, the syringe pump 200 will move the drive head to press the plunger of the syringe 206. The rate is controlled by the syringe pump 200 based on the programmed parameter (e.g., desired rate) and type of syringe.

Syringe pumps do not typically experience any upstream occlusion conditions because the fluid to be infused is housed in the syringe 206 and is pushed into an administration set 210 by way of the plunger 202. Downstream occlusion conditions can be detected by a force sensor housed in or upon a pump system 212 according to the methods described here, which are readily applied to syringe pumps. The force sensor measures the force exerted by the drive head 204 of the syringe pump on the syringe plunger 202.

In some implementations, the syringe pump may include a high resolution pressure sensor that interfaces with a pressure disc (not shown) on the syringe administration set. The pressure disc provides a relatively large area in contact with the pressure sensor. This allows the pressure sensor to measure the pressure inside the administration set more directly (not through the syringe plunger head) and with higher resolution and higher accuracy compared with the drive head force sensor. The measurements from this pressure sensor and the drive head force sensor can be used independently or in conjunction with each other to detect an occlusion condition in a syringe pump.

In some implementations, the syringe pump includes a back-off function that provides pressure relief, allowing the syringe to reduce a volume of a bolus after release of the occlusion.

In an infusion pump, various components that lie in an infusion path such as administration set, cannula, filters, and valves exhibit both resistance and compliance. In normal operation when there is no occlusion, the pump generates a pressure, termed a working pressure, to overcome the resistance of these and other components in the infusion path. The working pressure depends on a flow rate of the fluid in the infusion path. In particular, $$\text{Working pressure} = \text{Resistance} \times \text{Flow rate} \quad (1)$$

Figure 3A:
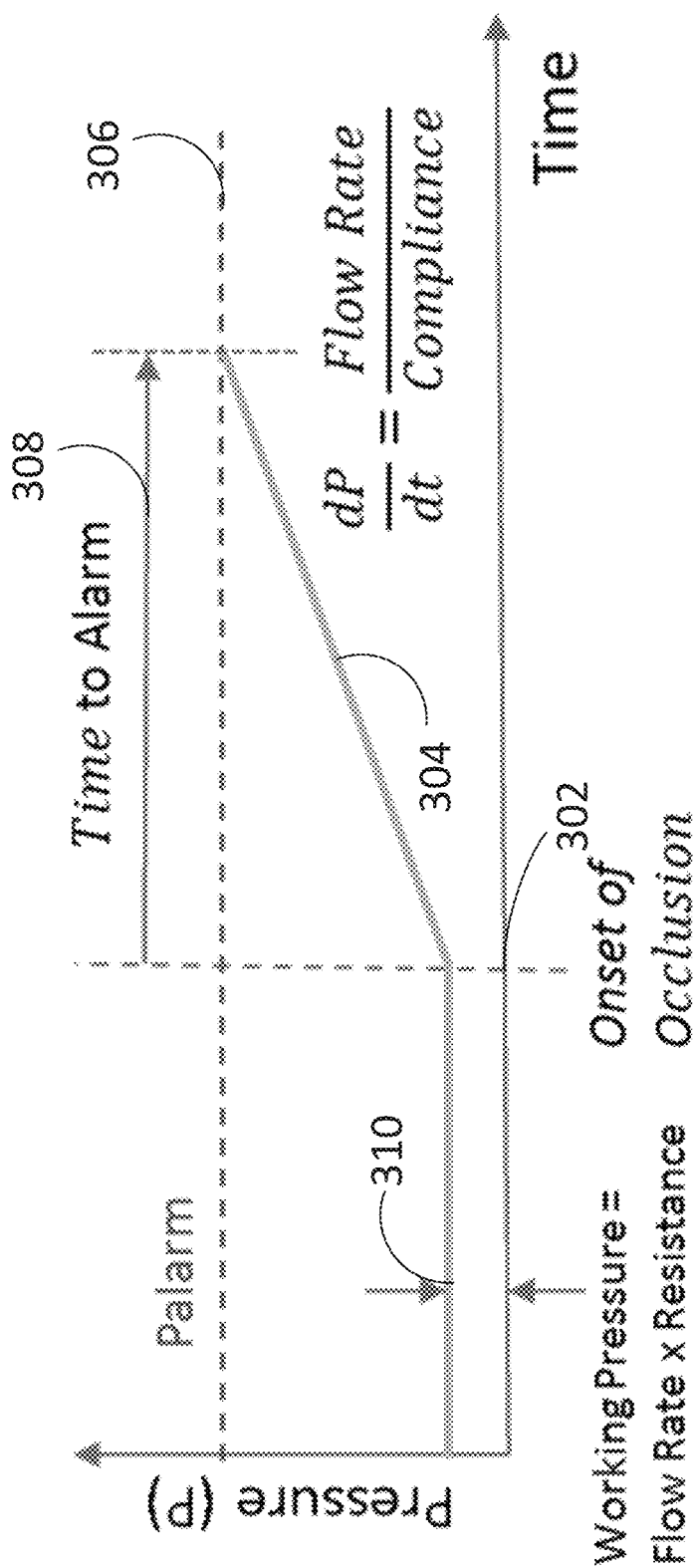
FIG. 3A depicts a method that uses a fixed point occlusion threshold for detecting a downstream occlusion.

FIG. 3A shows an example fluidic pressure profile of an infusion path as a function of time, and how some methods detect a downstream occlusion condition, according to various aspects of the subject technology. A working pressure 310 is the usual fluidic pressure in the infusion path under normal operation of the infusion pump. When an occlusion occurs, at a time 302, a fluidic pressure (P) in the infusion path rises along a slope 304 until the fluidic pressure reaches a set occlusion threshold 306 ($P_{alarm}$) and the pump sounds an occlusion alarm. In general, a rate of pressure increase $$\left(\frac{dP}{dt}\right)$$

depends on the flow rate and the compliance of the administration set, the pump, or syringe in the syringe pump, and other components in the infusion path. Compliance is the inverse of stiffness (which is a measure of the resistance offered by an elastic body to deformation), and can be measured in units of meters per newton.

$$\frac{dP}{dt} = \frac{\text{flow rate}}{\text{compliance}} \quad (2)$$

A time to alarm (TTA) 308, is the time from the onset of occlusion at the time 302, until the infusion path reaches the fluidic pressure of the set occlusion threshold 306, $P_{alarm}$. The TTA 308 depends on the set occlusion threshold 306 $P_{alarm}$ and the compliance of the administration set, the pump, or syringe in the syringe pump, and other components in the infusion path.

$$\text{Time of Alarm}(TTA) = (P_{alarm} - \text{working pressure}) \times \frac{\text{compliance}}{\text{flow rate}} \quad (3)$$

According to Equation (3), the TTA 308 increases at lower flow rates and/or for larger compliance values.

Figure 3B:
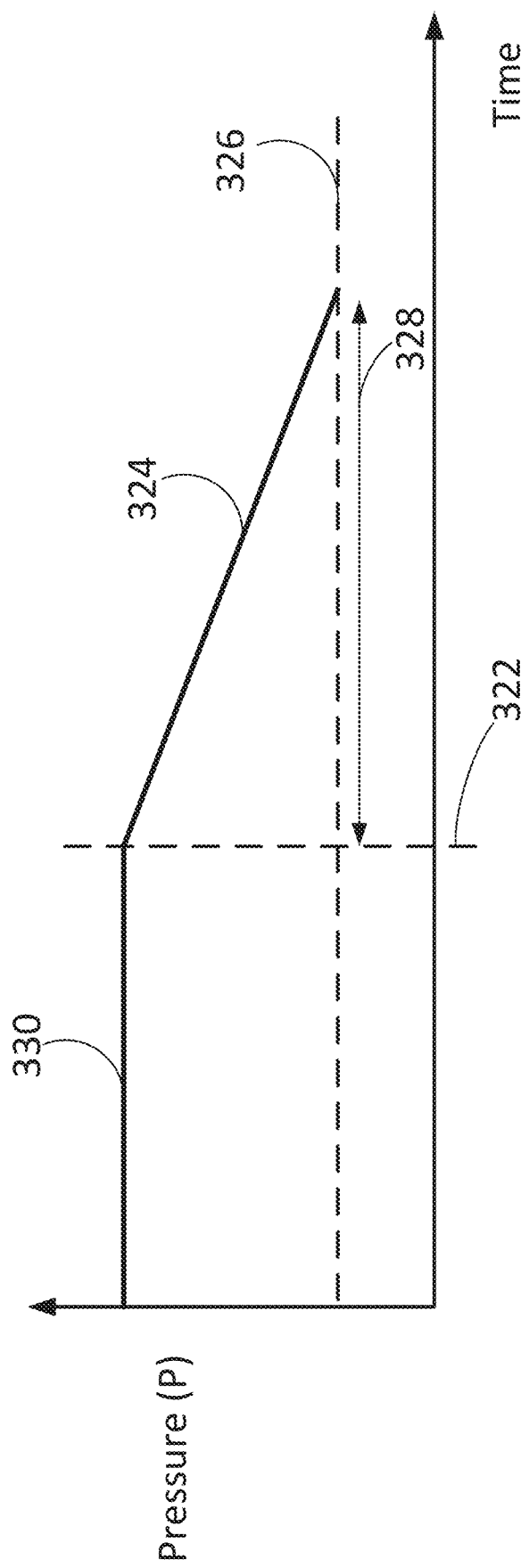
FIG. 3B depicts a method that uses a fixed point occlusion threshold for detecting an upstream occlusion.

FIG. 3B shows an example fluidic pressure profile of an infusion path as a function of time, and how some methods detect an upstream occlusion condition, according to various aspects of the subject technology. A working pressure 330 is the usual upstream fluidic pressure in the infusion path under normal operation of the infusion pump. When an occlusion occurs, at a time 322, a fluidic pressure (P) in the infusion path decreases along a slope 324 until the fluidic pressure reaches the set upstream occlusion threshold 326 ($P_{alarm}$) and the pump sounds an occlusion alarm. As at downstream fluidic pressures, a rate of pressure decrease $$\left(\frac{dP}{dt}\right)$$

depends on the flow rate and the compliance of the administration set, the pump, or syringe in the syringe pump, and other components in the infusion path. The pressure slope $$\frac{dP}{dt}$$

is negative for upstream fluidic pressure as show in FIG. 3B. In contrast, the pressure slope is positive for downstream fluidic pressures as shown in FIG. 3A. The TTA 328 is the time from the onset of upstream occlusion to the time the fluidic pressure drops to the set upstream occlusion threshold 326.

The methods and systems described in FIGS. 4-7 detect occlusion conditions in infusion devices earlier (e.g., much earlier) than methods that operate according to FIGS. 3A and 3B. As shown in FIGS. 3A and 3B, measured dynamic pressures (or forces) behave differently when under occlusion conditions (after the time 302 in FIG. 3A, and after the time 322 in FIG. 3B) compared with normal infusion conditions (before the time 302 and 322 in FIGS. 3A and 3B, respectively) when no occlusion exists. Even though FIGS. 4 and 5 focus mainly on the detection of downstream occlusions, the disclosed methods are applicable also to upstream occlusion detection without any loss of generality.

In normal operation (e.g., when there is no occlusion), a pressure measured along the infusion path varies directly with the flow rate, according to Equation (1). When the pump changes between two different flow rates (e.g., $F_1$ and $F_2$), the corresponding measured pressure (or force) also changes between two different values (e.g., $P_1$ and $P_2$).

Figure 4:
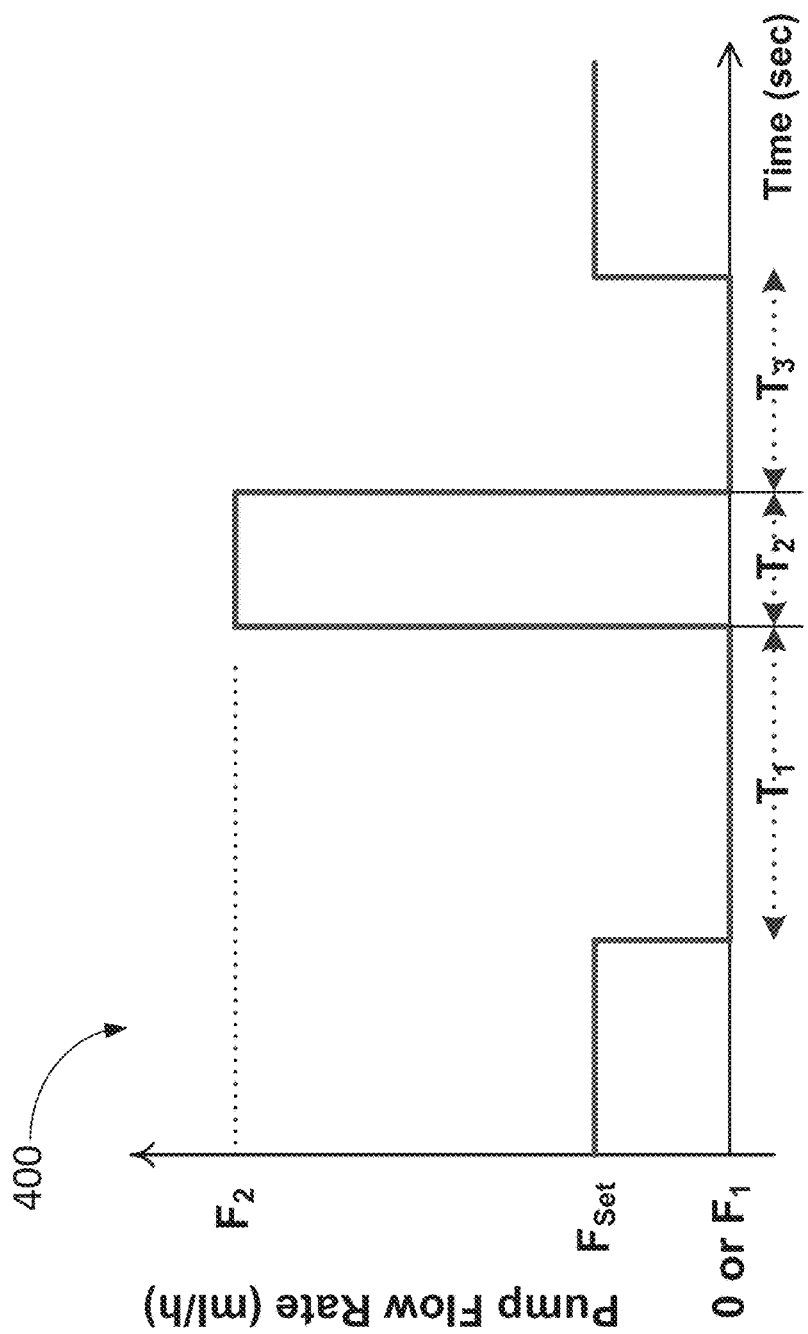
FIG. 4 depicts a flow rate profile according to aspects of the subject technology.
Figure 5A:
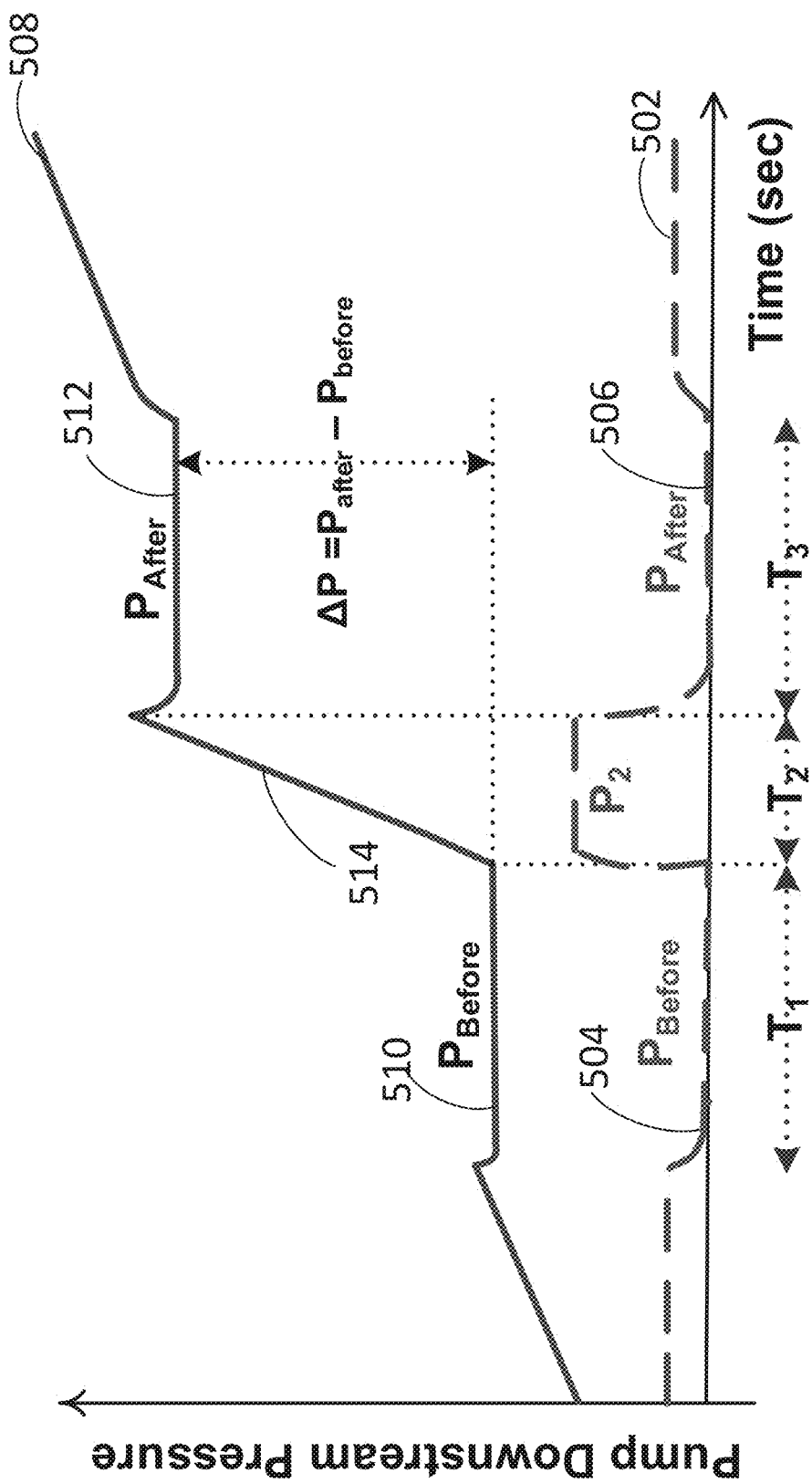
FIG. 5A depicts downstream pump pressure (or force) profiles for the flow rate profile shown in FIG. 4.

If the flow rate changes from $F_1$ to $F_2$ and back to $F_1$, as shown in FIG. 4, according to various aspects of the subject technology, the measured pressure will change from $P_1$ to $P_2$ and then back to $P_1$, as shown in FIG. 5A. FIG. 4 shows a pump flow rate profile 400. In the pump flow rate profile 400, the pump flow rate is set at $F_1$ (or 0 ml/hour) during a first time interval $T_1$. During a second time interview $T_2$, the pump flow rate is set at $F_2$, and during a third time interval $T_3$, the pump flow rate is set at $F_1$ again.

In general, the pump can set a third flow rate $F_3$ during the third time interval $T_3$. In some implementations, the third flow rate $F_3$ equals to the first flow rate $F_1$. In some implementations, the first flow rate $F_1$ (and the third flow rate $F_3$) is 0 ml/hour. The pump flow rate profile 400 operates at a set flow rate $F_{set}$ prior to the first time interval $T_1$ and after the third time interval $T_3$.

A value of the fluidic pressure remains approximately constant (e.g., flat) within each of these intervals: an approximately constant value of $P_1$ over the first time interval $T_1$ when the system operates at the first flow rate ($F_1$), and an approximately constant value of $P_2$ over the second time interval $T_2$ when the system operates at the second flow rate ($F_2$).

When there is an occlusion condition, the measured pressure (or force) signal may behave differently. For a given flow rate, when there is a downstream occlusion condition, the fluidic pressure does not remain constant, but rises gradually. The pressure rise ($\Delta P$) over a particular time interval is directly proportional to the amount of volume ($\Delta V$) of fluid infused over that interval, i.e., $$\Delta P = \frac{\Delta V}{\text{compliance}} \quad (4)$$

where $\Delta V$=flow rate×time interval of infusion

The methods and systems disclosed here involve monitoring the pressure (or force) while changing the flow rate over a short period of time. In some implementations, the methods include the following steps:

First, the infusion device (e.g., an infusion pump) changes a flow rate from the programmed (set) rate, $F_{set}$, to $F_1$ during a first time interval $T_1$. $F_1$ is either 0 ml/h or a rate much smaller than $F_{Set}$.

Second, the infusion device then changes the flow rate from $F_1$ to $F_2$ during a second time interval $T_2$. $F_2$ is a flow rate much larger than $F_{set}$. $T_2$ is between tens of milliseconds to one second. The values of $F_2$ and $T_2$ are chosen such that the volume ($\Delta V = F_2 \times T_2$) infused over $T_2$ is, at least, a few microliters.

Third, the infusion device then changes the flow rate from $F_2$ to $F_3$ (e.g., $F_3 = F_1$) for a third time interval $T_3$. In some implementations, the values of $F_1$, $F_2$, $T_1$, $T_2$, and $T_3$ are chosen such that:

$$(T_1+T_2+T_3) \times F_{set} = [(T_1+T_3) \times F_1 + (T_2 \times F_2)] \quad (5)$$

For $F_1 = 0$ ml/hour, then equation (5) becomes:

$$(T_1+T_2+T_3) \times F_{set} = T_2 \times F_2 \quad (6)$$

Fourth, at the end of $T_3$, the infusion device returns to a flow rate of $F_{Set}$ and continues infusion as normal.

The flow rate profile described in the four steps above is illustrated in FIG. 4, for the case where $F_1 = 0$ ml/hour. FIG. 5A shows a dashed curve 502 of the corresponding downstream fluidic pressure (or force) profile in the infusion path during normal infusion with no downstream occlusion condition, according to various aspects of the subject technology, when subject to the flow rate profile 400 shown in FIG. 4. A value of a pressure 504 before (e.g., $P_{before}$) and a value of a pressure 506 after (e.g., $P_{after}$) the time interval $T_2$ is the same. The change in pressure between time intervals $T_1$ and $T_2$ (e.g., $\Delta P = P_2 - P_{before}$) in the absence of occlusion is given by:

$$(P_2 - P_{before}) = \text{flow rate} \times \text{resistance} \quad (7)$$

where resistance refers to the resistance introduced by the administration set, the cannula, the subject's vein, valves, and other components along the infusion path.

In some implementations, the flow rates $F_1$ and/or $F_3$ may be set to negative values. For example, when flow rates have negative values, the infusion pump moves the fluid in a reverse direction for a (e.g., short) period of time (e.g., during $T_1$ and/or $T_3$). A slope of the rise of the fluidic pressure during $T_2$ depends on the flow rate $F_2$ (during $T_2$), which is independent of $F_1$. Based on Equation 5, $F_2$ may be higher and the slope during $T_2$ may also be larger, for a negative $F_1$.

In FIG. 5A, a curve 508 shows the downstream fluidic pressure (or force) profile in the infusion path under a downstream occlusion condition. The pressure flow profile during $T_1$ (a pressure 510) and $T_3$ (a pressure 512) is flat because $F_1 = 0$ ml/hour in the flow rate profile 400 shown in FIG. 4. A pressure 514 rises rapidly during $T_2$ due to the large flow rate $F_2$. The pressure 512 after ($P_{after}$) the time interval $T_2$ is larger than the pressure 510 before ($P_{before}$) the time interval $T_2$. The change in pressure, $\Delta P$, is directly proportional to the volume ($F_2 \times T_2$) pumped during time interval of $T_2$. That is, $$\Delta P = (P_{after} - P_{before}) = \frac{T_2 \times F_2}{\text{compliance}} \quad (8)$$

The pressure change, $\Delta P$, is controlled by adjusting $F_2$ and $T_2$, where $F_2 \times T_2 = \Delta V$, the volume infused during time interval $T_2$. $\Delta V$ is typically a few microliters.

The pressure curves 502 and 508 shown in FIG. 5A are for demonstration purposes and are not drawn to scale. A small drop of pressure at the beginning of $T_1$ and the beginning of $T_3$ in the curve 508 is due to the lower flow rate ($F_1$) during periods $T_1$ and $T_3$ (e.g., $F_1 < F_2$ or $F_{set}$). The lower flow rate means that less pressure is required to overcome the resistance in the infusion path.

Syringe pumps and LVP pump both exhibit downstream pressure profiles similar to curves 502 and 508.

The pump flow rate profile 400 depicted in FIG. 4 includes a period of time $T_1$ in which the flow is paused (having a flow rate $F_1$ that is 0 ml/hour during the period of time $T_1$) followed by a period of time $T_2$ that includes a burst of fluid flow (having a flow rate $F_2 > 0$ ml/hour during the period of time $T_2$), followed by a second pause period $T_3$ (having a flow rate $F_1$ that is 0 ml/hour during the second pause period $T_3$). In some implementations, the burst helps to maintain continuity for the volume of fluid delivered, while simultaneously allowing an evaluation of the pressure difference. In some implementations, as shown in FIG. 5B, an alternative pump flow rate profile omits the burst.

Figure 5B:
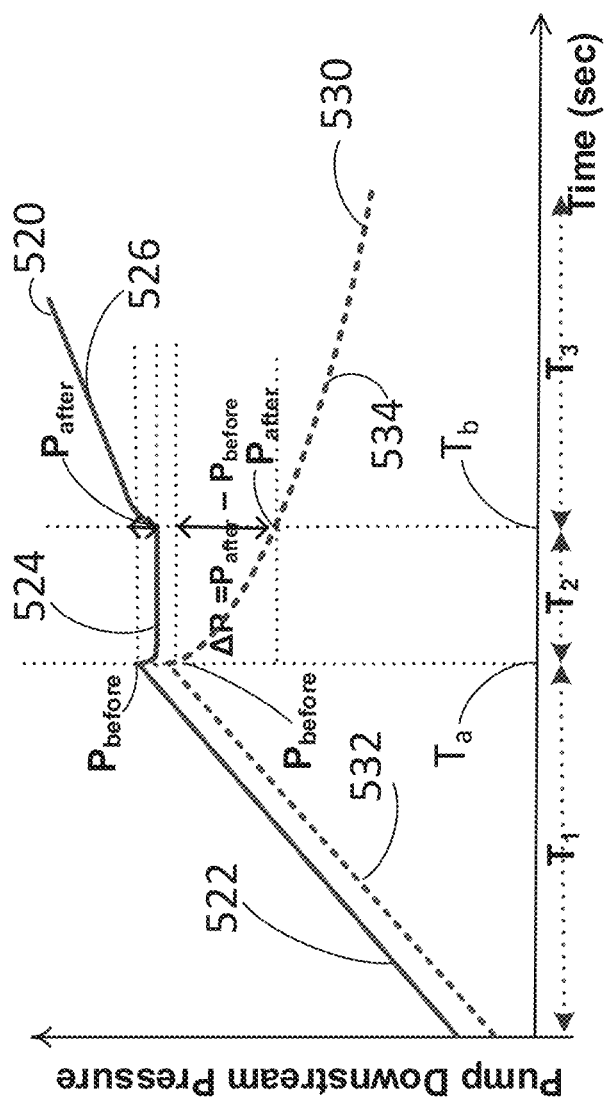
FIG. 5B depicts a downstream pump pressure (or force) profiles for an alternative flow rate profile.

FIG. 5B depicts a downstream pump pressure (or force) profiles for an alternative flow rate profile. A curve 520, which includes a flat portion having a substantially constant pressure 524, shows the downstream fluidic pressure (or force) profile in the infusion path under a downstream occlusion condition. The pressure profile during $T_1$ (spanning a pressure range 522) and $T_3$ (spanning a pressure range 526) rises due to the non-zero flow rate in the alternative pump flow rate profile. The pressure range 526 after the time interval $T_2$ is larger than the pressure range 522 before the time interval $T_2$ due to the presence of the downstream occlusion condition. A first pressure measurement ($P_{before}$) is taken at $T_a$ when the pump stops pumping (flow rate=0 ml/hour). A second pressure measurement ($P_{after}$) is taken at $T_b$. The two measurements are compared and a difference in pressure is determined. In response to determining that a difference between the two measurement is smaller than a threshold (e.g., there is little or no difference between the two measurements), the system will signal that an occlusion is detected, and an alarm is sounded or displayed. In response to detecting a difference between the two measurements, (e.g., larger than a threshold), the system will determine that there is no occlusion and the pump resumes pumping fluid.

FIG. 5B shows a dashed curve 530 of the corresponding downstream fluidic pressure (or force) profile in the infusion path during normal infusion with no downstream occlusion condition, according to various aspects of the subject technology, when subject to the alternative pump flow rate profile. A change in pressure $\Delta P$ between $P_{before}$ at $T_a$ and $P_{after}$ at $T_b$ is much larger compared to the change in pressure $\Delta P$ when there is no occlusion. When the change in pressure, $\Delta P$, meets or is less than a threshold (e.g., $\Delta P \sim 0$), an occlusion is likely. By omitting a pump flow rate profile that includes a burst of fluid flow (e.g., the pump flow rate profile 400 having a flow rate $F_2$ during $T_2$), the system may arrive at an occlusion detection signal faster than when using the burst mode. An occlusion detection mode that utilizes a pump flow rate profile that includes a burst of fluid flow after a period of time in which the flow is paused is termed "with burst." An occlusion detection mode that utilizes a pump flow rate profile that omits a burst of fluid flow after a period of time in which the flow is paused is termed "without burst." A tradeoff between these two occlusion detection modes may include, for example, better fluid continuity for the "with burst" occlusion detection mode, and a higher speed of detection for the "without burst" occlusion detection mode.

In some implementations, the two occlusion detection modes ("with burst" and "without burst") may be dynamically selected. For example, certain drugs or care areas (e.g., neonatal intensive care unit) may have critical delivery characteristics whereby continuity is an important safety factor. For these drugs or care areas, the system may use the "with burst" mode to ensure fluid continuity. For other drugs or care areas, the system may use the "without burst" mode. The indication of which occlusion detection mode is recommended for usage may be included in a drug library entry for the drug or care area configuration for the infusion system. Once the care area or drug is programmed to the pump, the appropriate occlusion algorithm (e.g., including the recommended occlusion detection mode) may be activated.

Figure 6:
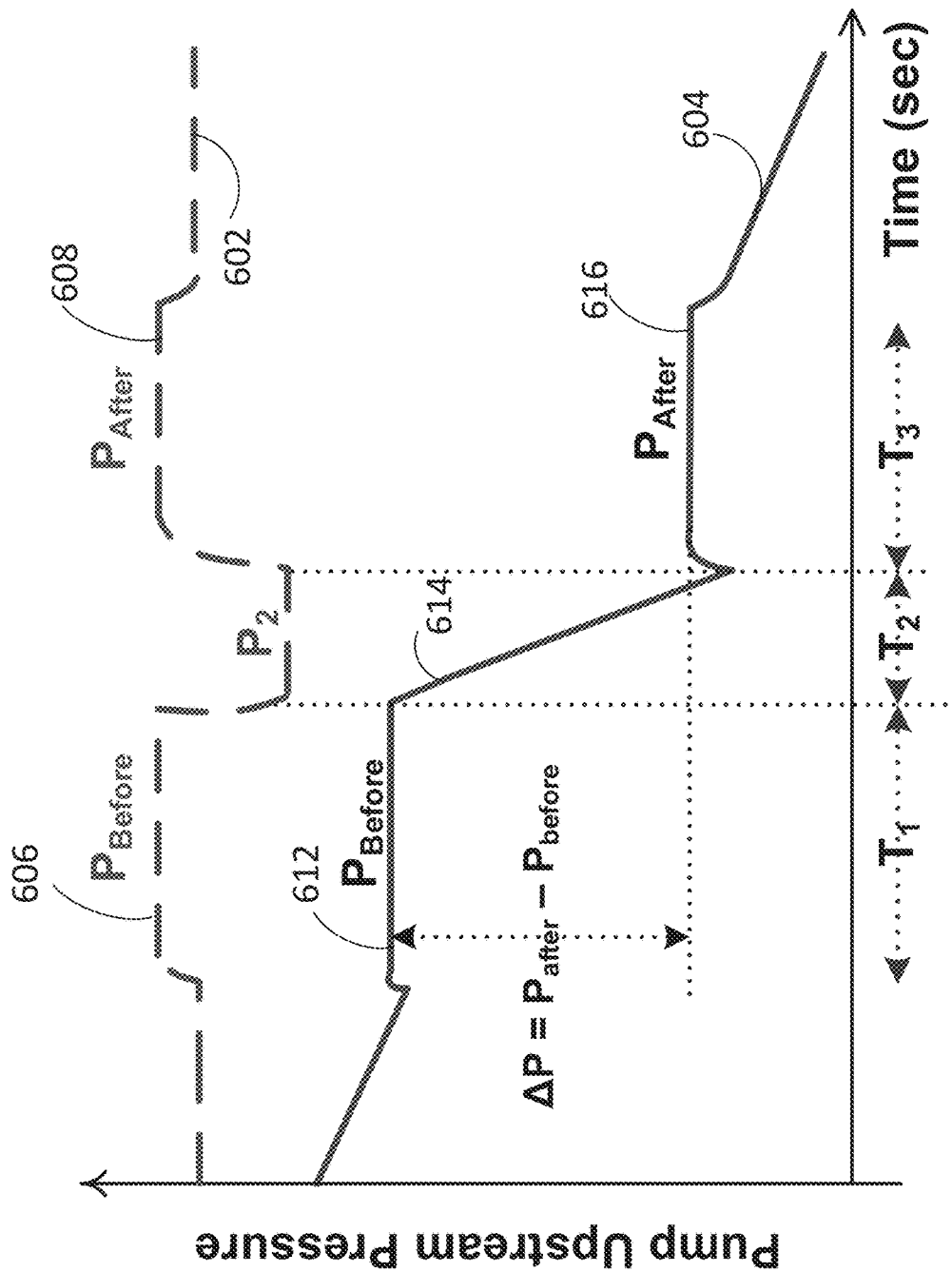
FIG. 6 depicts upstream pump pressure (or force) profiles in a LVP pump for the flow rate profile shown in FIG. 4.

FIG. 6 shows upstream fluidic pressure curves 602 and 604, according to various aspects of the subject technology. The curves are for illustration purposes and are not drawn to scale. The upstream fluidic pressure curve 602 is recorded under normal functioning of the infusion device (e.g., no occlusion occurs). In contrast, the upstream fluidic pressure curve 604 is recorded when an upstream occlusion condition exists. In some implementations, LVP pumps display similar upstream pressure profiles as curves 602 and 604, under normal and occlusion conditions, respectively. In general, when upstream occlusion conditions occurs, there is relative negative pressure (e.g., vacuum) generated in the fluidic path between the point of the upstream occlusion and the pump (or the upstream pressure sensor).

The fluidic pressure curve 602 shows a pressure 606 before ($P_{before}$) and a pressure 608 after ($P_{after}$) time interval $T_2$ are the same.

The upstream pressure profile under upstream occlusion condition is displayed as the fluidic pressure curve 604. In some implementations, a flow rate during the first time interval $T_1$ and a third time interval $T_3$ are both zero (i.e., $F_1=0$ ml/hour and $F_1=0$ ml/hour). Under such conditions, the pressure profile (e.g., 612 and 616) during $T_1$ and $T_3$ is flat. The pressure falls rapidly during $T_2$ due to the large flow rate $F_2$ (e.g., as shown in FIG. 4). In some implementations, the falling pressure starts to approach vacuum conditions in the fluidic channel. As a result, the pressure after ($P_{after}$) time interval $T_2$ is lower than the pressure before ($P_{before}$) the time interval of $T_2$. The change in pressure, $\Delta P$, is directly proportional to the volume ($F_2 \times T_2$) pumped during time interval of $T_2$. That is, $$\Delta P = (P_{after} - P_{before}) = \frac{-(T_2 \times F_2)}{\text{compliance}} \quad (9)$$

The pressure change, $\Delta P$, is controlled by adjusting $F_2$ and $T_2$, where a product of $F_2$ and $T_2$ reflects the volume of fluid, $\Delta V$, infused during the time interval $T_2$ (i.e., $F_2 \times T_2 = \Delta V$). $\Delta V$ is typically a few microliters.

The small rise of pressure at the beginning of both $T_1$ and $T_3$ in FIG. 6 is due to the lower flow rate ($F_1$) during the time intervals $T_1$ and $T_3$ (e.g., $F_1 < F_2$ or $F_{set}$). The lower flow rate means that less negative pressure is required to pull the fluid from upstream of the pump. Hence the small amount of pressure increase at the beginning of $T_1$ and $T_3$.

In some implementations, the $P_{after}$ and $P_{before}$ pressure values for downstream and/or upstream fluid flows are averaged by measuring the fluidic pressure over a selected duration (e.g., a few hundred of milliseconds) to average out the noise associated with the pressure detection, producing higher signal to noise ratios.

A determination is made regarding whether an occlusion condition exists by selecting a suitable threshold for the pressure differential $\Delta P$ (e.g., $P_{after} - P_{before}$). If an absolute value (i.e., magnitude) of the measured $\Delta P$ (i.e., $|\Delta P|$) exceeds the threshold, then an occlusion condition exists. A magnitude of the measured pressure difference is always positive. Thus, an upstream occlusion condition exists when a magnitude of the measured pressure difference $\Delta P$ (i.e., $P_{after} - P_{before}$) is greater than a set upstream threshold (e.g., $\text{Threshold}_{upstream}$). In some implementations, machine-learning is implemented on a server (or on a PCU with a larger memory and/or CPU resources) and is used to identify occlusion in pressure signals received from the pump. For example, machine learning techniques are used to adaptively adjust the threshold (e.g., between $P_{before}$ and $P_{after}$). In this way, the methods and systems described herein intelligently adjust a threshold, instead of using a fixed value for all pumps. In some implementations, machine learning includes using training data sets of values of threshold associated with known occlusion conditions to train models used to determine if an occlusion exists.

For downstream fluidic pressures, if $\Delta P$ (e.g., $P_{after} - P_{before}$) is larger than $\text{Threshold}_{downstream}$, then a downstream occlusion condition exists. For upstream fluidic pressures, if $\Delta P$ is less than $\text{Threshold}_{upstream}$, then an upstream occlusion condition exists. Equivalently, for upstream fluidic pressures, if an absolute value of the pressure difference, $|\Delta P|$ is larger than an absolute value of $\text{Threshold}_{upstream}$ (e.g., $|\text{Threshold}_{upstream}|$), an upstream occlusion condition exists. In general, $\text{Threshold}_{downstream}$ is a positive value and $\text{Threshold}_{upstream}$ is a negative value. But $|\text{Threshold}_{upstream}|$, the absolute value/magnitude of the upstream threshold, is positive.

In some implementations, to gain confidence in measured pressure signatures recorded in the infusion path, the flow rate profile 400 is repeatedly generated for multiple measurements (e.g., shown in FIG. 5 or 6) to be made before and after the time interval $T_2$. In some implementations, these measurements record upstream pressure signatures. In some implementations, these measurements record downstream pressure signatures. In some implementations, these measurements record both upstream and downstream pressure signatures (e.g., simultaneously). In some implementations, $\Delta P$ values in Equations (8) and (9) are the averages of multiple measurements.

In some implementations, the pump activates an appropriate flow profile, such as the flow rate profile 400 shown in FIG. 4, to create the downstream and upstream pressure signatures discussed above. In some implementations, the trigger for the pump activating (e.g., generating) the flow rate profile is the detection of a rising slope for downstream fluidic pressures or the detection of a falling slope for upstream pressures. In some implementations, the pump generates the flow rate profile (e.g., the flow rate profile 400) periodically (e.g., every few minutes). In some implementations, the pump takes about a second to generate the flow rate profile 400 in the infusion path. In some implementations, the pump uses slope changes as a trigger and also periodically generates the flow rate profile 400.

Figure 7:
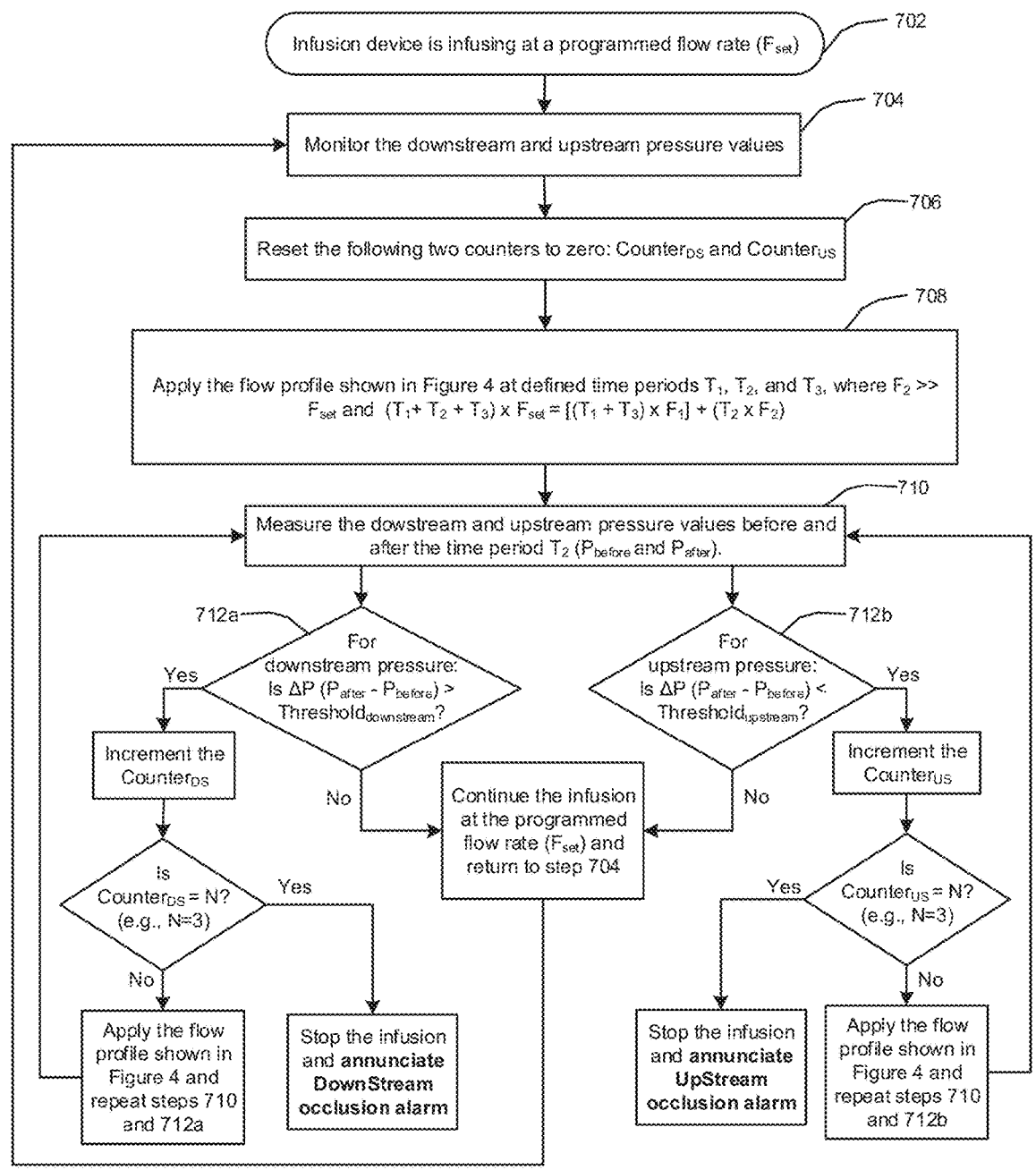
FIG. 7 is flow chart that illustrates a method of detecting an occlusion according to aspects of the subject technology.

FIG. 7 shows a flow chart for a method 700, according to various aspects of the subject technology. The method 700 may be performed or coordinated by one or more coordination devices such as the infusion pump, an infusion pump module, a patient care unit (PCU) associated with the infusion pump delivering the fluid, a server, an infusion pump controller, or the like.

At a step 702, the coordination device begins infusing the fluid at a programmed flow rate $F_{set}$. At a subsequent step 704, the coordination device monitors both downstream and upstream pressure values. In some implementations, the downstream pressure values are measured using a downstream pressure sensor. In some implementations, the upstream pressure values are measured using an upstream pressure sensor. The methods described herein are applicable to all LVPs regardless of their pressure sensor configurations. For example, most LVP pumps have two pressure sensors, one for sensing upstream pressures and a second one for sensing downstream pressure. Some pumps do not have an upstream sensor and only have a downstream pressure sensor.

The methods described herein are also applicable to LVP pumps with only one pressure sensor that measures both the downstream and upstream pressures (just not at the same time). For example, the flow profile during the downstream and upstream measurements is applied separately. In a step 706, one counter for upstream occlusion condition (e.g., Counter$_{us}$) is set to zero, and another counter (e.g., Counter$_{ds}$) for downstream occlusion conditions is set to zero.

At a later step 708, the coordination device applies a flow profile similar to the one shown in FIG. 4 over a first time interval (e.g., $T_1$), a second time interval (e.g., $T_2$), and a third time interval (e.g., $T_3$). The flow rate profile includes a second flow rate $F_2$ (e.g., at the second time interval) that is much greater than the programmed flow rate $F_{set}$. In addition, the total volume of fluid flow over the sum of the first, second, and third time intervals are the same under the programmed flow rate as under the flow rate profile (for the first flow rate $F_1$, the second flow rate $F_2$, and the third flow rate $F_3$). For example, when the first flow rate is equal to the third flow rate, the following equation holds: $(T_1+T_2+T_3) \times F_{set}=[(T_1+T_3)\times F_1]+(T_2 \times F_2)$. More generally, the following equation holds: $(T_1+T_2+T_3)\times F_{set}=(T_1 \times F_1)+(T_2 \times F_2)+(T_3 \times F_3)$.

In some implementations, the flow profile applied at the step 708 is applied periodically during (e.g., throughout) the infusion. In some implementations, the infusion device applies the flow profile at step 708 when a temporal variation of fluidic pressure (e.g., a slope of the fluidic pressure or the "pressure slope") changes faster than a specified threshold. In other words, the pressure slope triggers the application of the flow profile at step 708. The fluidic pressure can be downstream or upstream fluidic pressure.

In a step 710, the coordination device measures downstream and upstream pressure values before and after the time interval having the high flow rate (e.g., the second time interval $T_2$ shown in FIG. 4, when the flow rate is $F_2$), yielding $P_{before}$ and $P_{after}$, respectively.

The coordination device processes the measured downstream and upstream fluidic pressures separately.

Downstream Fluidic Pressure

In a step 712a, the coordination device computes a difference in downstream fluidic pressure (or pressure differential) $\Delta P$ between $P_{before}$ and $P_{after}$. In some implementations, for downstream pressure, the pressure differential $\Delta P$ is computed by subtracting $P_{before}$ from $P_{after}$ (i.e., $P_{after}-P_{before}$). As shown in FIG. 5A, when a downstream occlusion condition exists, $P_{after}$ is larger than $P_{before}$, resulting in a positive pressure differential $\Delta P$.

When this difference in pressure $\Delta P$ is larger than a set threshold for downstream fluidic pressures (Threshold$_{downstream}$), the counter for downstream occlusion condition is incremented. The coordination device then checks if a value of the counter for downstream occlusion condition is greater than a set number. In some implementations, the set number is 3, indicating the number of measurements of downstream occlusion conditions before an alarm sounds. If the value of the counter for the downstream occlusion condition is smaller than the set number, the coordination device once again applies the flow profile shown in FIG. 4 and repeats the steps 710 and 712a. In contrast, if the value of the counter for the downstream occlusion condition is greater than the set number, the infusion process is stopped, and the coordination device annunciates a downstream occlusion alarm.

When this difference in pressure $\Delta P$ is smaller than Threshold$_{downstream}$, the infusion device continues infusing at the programmed flow rate $F_{set}$, and return to the step 704.

Upstream Fluidic Pressure

In a step 712b, the coordination device computes a difference in upstream fluidic pressure (or pressure differential) $\Delta P$ between $P_{before}$ and $P_{after}$. In some implementations, for upstream pressure, the pressure differential $\Delta P$ is computed by subtracting $P_{before}$ from $P_{after}$ (i.e., $P_{after}-P_{before}$). As shown in FIG. 6, when an upstream occlusion condition exists, $P_{after}$ is smaller than $P_{before}$, resulting in a negative pressure differential $\Delta P$.

When this difference in pressure $\Delta P$ is smaller (i.e., more negative) than a set threshold for upstream fluidic pressures (Threshold$_{upstream}$), the counter for upstream occlusion condition is incremented.

In some implementations, a magnitude of the pressure differential is taken, and the absolute value of $\Delta P$ is compared against Threshold$_{upstream}$. In that case, the counter for upstream occlusion condition is incremented when $|\Delta P|$ is greater than Threshold$_{upstream}$. The coordination device then checks if a value of the counter for upstream occlusion condition is greater than a set number. In some implementations, this set number is same as the set number as for downstream occlusion condition. Alternatively, if there is a different tolerance for upstream occlusion conditions than for downstream occlusion condition, a different number is set. In some implementations, the set number is 3, indicating the number of measurements of upstream occlusion conditions before an alarm sounds. If the value of the counter for the upstream occlusion condition is smaller than the set number, the coordination device once again applies the flow profile shown in FIG. 4 and repeats the steps 710 and 712b. In contrast, if the value of the counter for the upstream occlusion condition is greater than the set number, the infusion process is stopped, and the coordination device annunciates an upstream occlusion alarm.

When this difference in pressure $\Delta P$ is smaller than Threshold$_{downstream}$, the infusion device continues infusing at the programmed flow rate $F_{set}$, and return to the step 704.

In some implementations, for example, as shown in FIGS. 8-12, an infusing device operating in burst mode at $F_{set}$, already generates the flow profile shown in FIG. 4, without additionally creating a separate sequence of flow rates $F_1$, $F_2$, and $F_3$. In such cases, the step 708 is optional.

FIGS. 8-12 provide an example that implements the methods described in the disclosure, according to various aspects of the subject technology. The example exploits an existing flow rate profile produced by a LVP pump. At flow rates below 40 ml/hour, a flow rate profile produced by the LVP pump is similar to the flow profile shown in FIG. 2, permitting a convenient demonstration of the feasibility of the methods described in the disclosure.

At flow rates below 40 ml/hour, the LVP pump works in burst mode. For example, in some implementations, each burst moves a stepper motor 25 steps. These 25 steps are completed over 25 milliseconds for a motor operating at 1 kHz. In some case, there are 200 bursts in one mechanism cycle.

Figure 8:
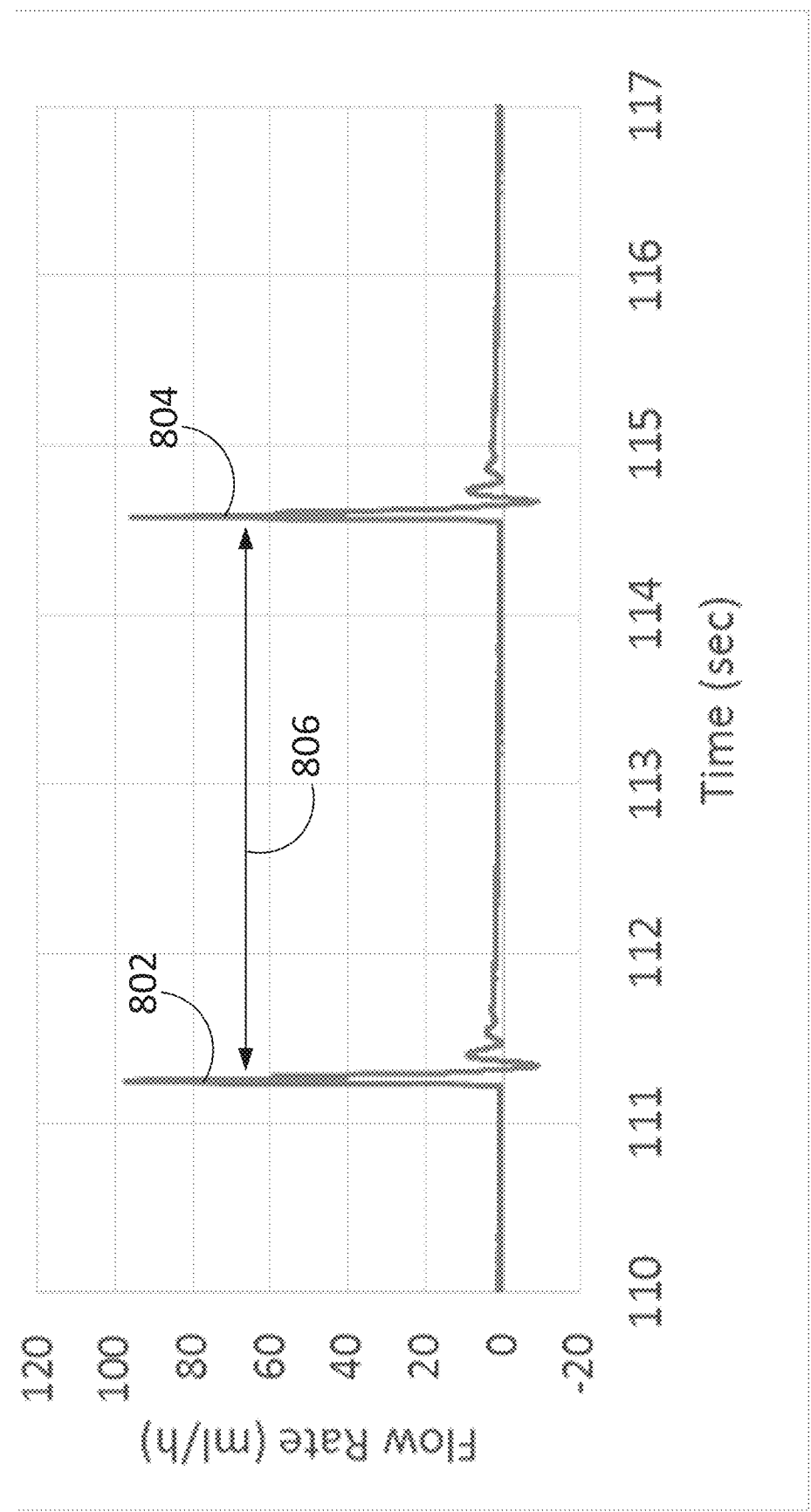
FIG. 8 shows two consecutive flow bursts at a programmed flow rate in an LVP pump.

FIG. 8 shows two consecutive flow bursts 802 and 806 at a flow rate of 1 ml/hour, according to various aspects of the subject technology. Each flow burst and its ripples last about 200 milliseconds. The volume infused at each burst in about 1-2 µL. The two flow bursts having peaks that are separated by a time interval 806. The period between the bursts is dependent on the flow rates. For example, it is about 3.25 seconds at a programmed flow rate 1 ml/hour. The flow rate between bursts 802 and 804 is 0 ml/hour. So each flow burst (e.g., flow burst 802 and flow burst 804) is similar to a high flow rate (e.g., $T_2$) shown in FIG. 4. The example shown in FIG. 8 takes advantage of the flow rate profile to measure the pressure before and after each burst in order to differentiate normal operation of the infusion pump (e.g., with no occlusion) from downstream or upstream occlusion conditions.

Figure 9:
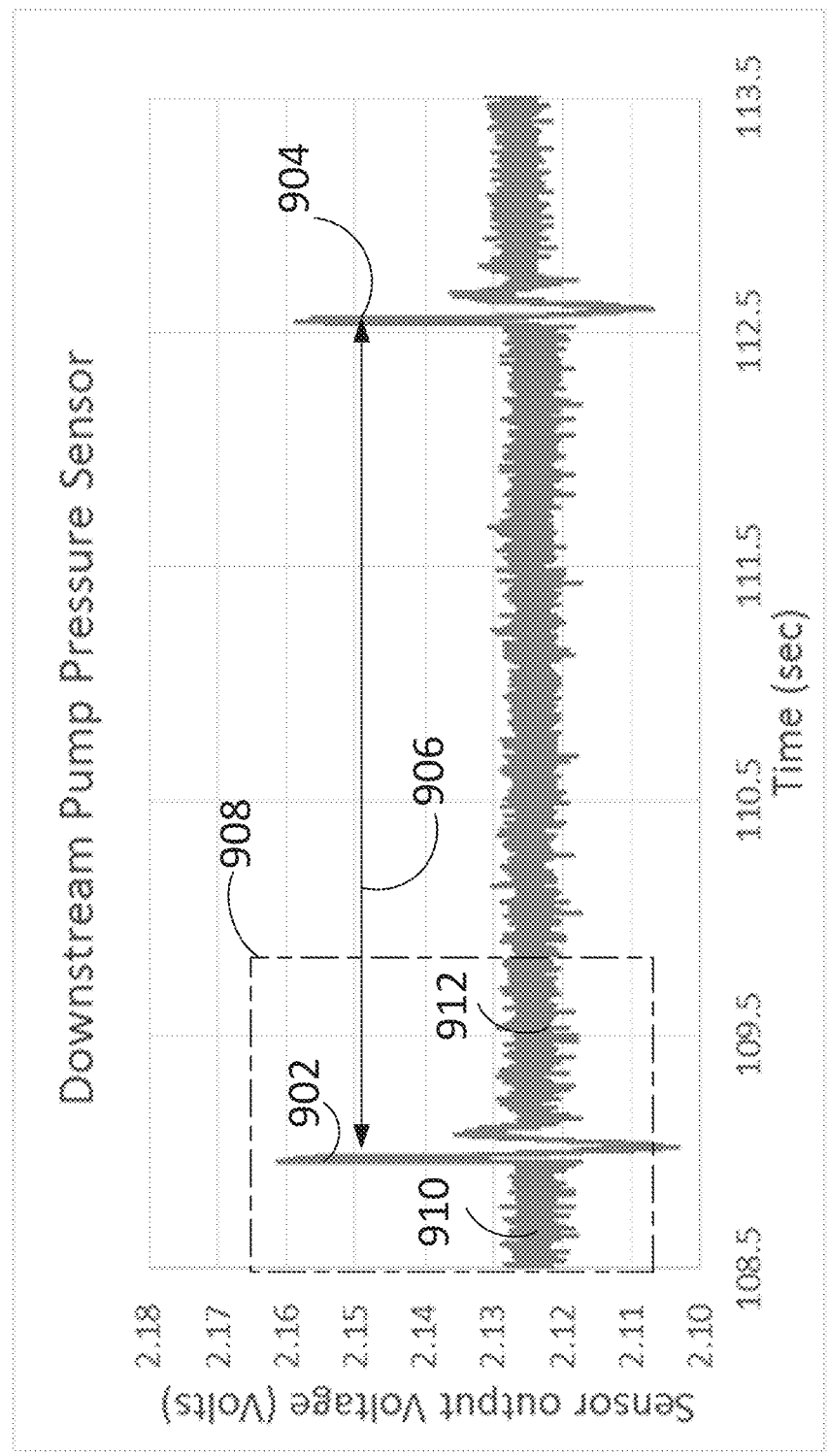
FIG. 9 shows an output of a downstream pump pressure sensor in the LVP pump for the flow rate profile shown in FIG. 8 during normal operation when there is no occlusion condition.
Figure 10A:
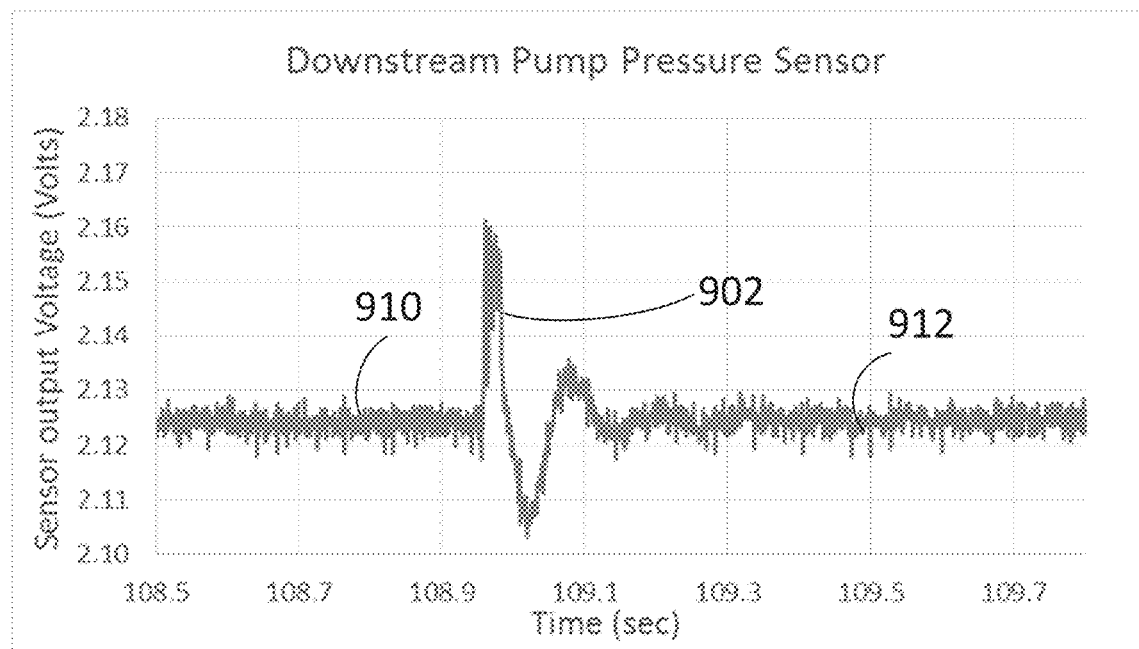
FIG. 10A is an enlarged view of a portion of FIG. 9.
Figure 10B:
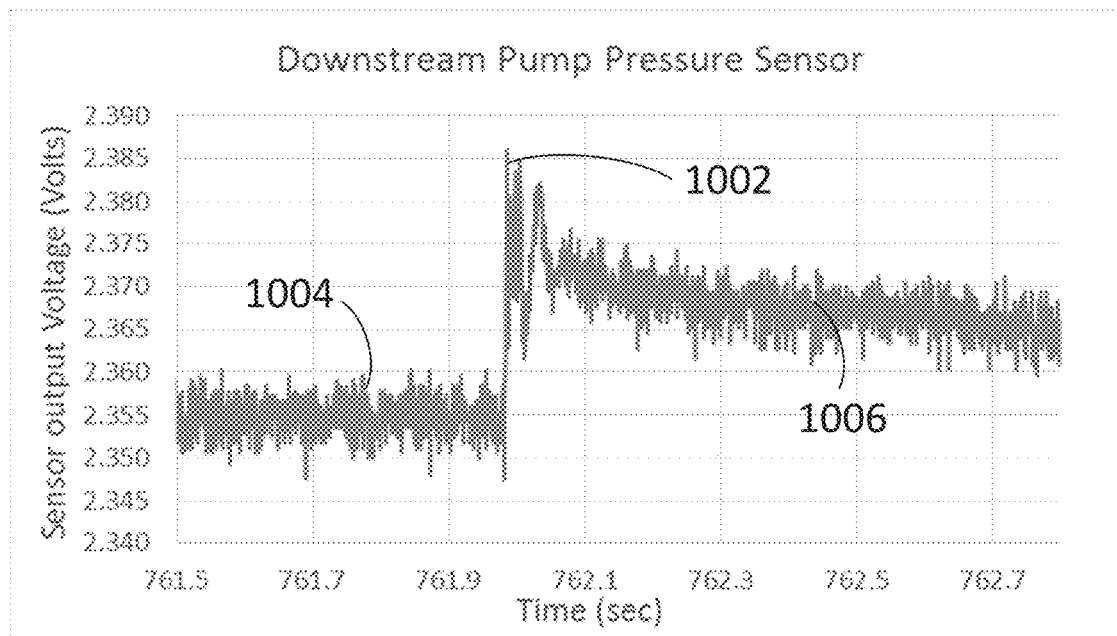
FIG. 10B shows an output of a downstream pump pressure sensor in the LVP pump for the flow rate profile shown in FIG. 8 under a downstream occlusion condition.

FIGS. 9 and 10B show the corresponding measured downstream pump pressure profiles for the flow rate profile shown in FIG. 8 in normal operation (FIG. 9) and under downstream occlusion condition (FIG. 10B), according to various aspects of the subject technology. In FIG. 9, a first measured pressure spike 902 corresponds to the flow burst 802 shown in FIG. 8, and a second measured pressure spike 904 corresponds to the flow burst 804 shown in FIG. 8. The measured pressure spikes 902 and 904 are measured in volts, from a voltage output of the downstream pressure sensor. The two measured pressure spikes are separated by a time interval 906. FIG. 10A shows an expanded time scale representation of portion 908 shown in FIG. 9.

FIG. 10A and FIG. 10B are presented on the same time scale for ease of comparing pressure measurements under normal operation (FIG. 10A) and under a downstream occlusion condition (FIG. 10B).

Figure 11:
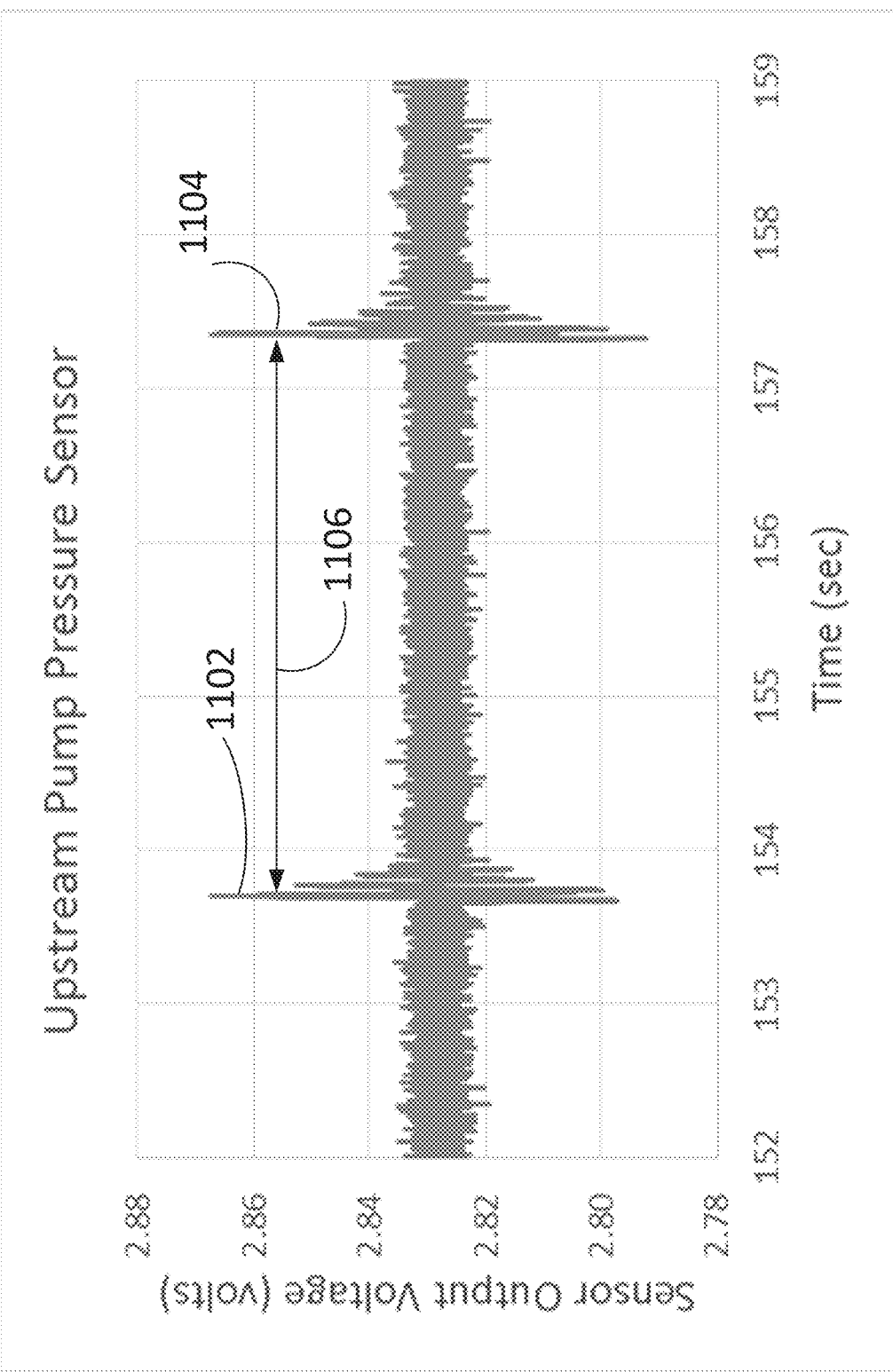
FIG. 11 shows an output of an upstream pressure sensor in LVP pump for the flow rate profile shown in FIG. 8 during normal operation when there is no occlusion condition.
Figure 12:
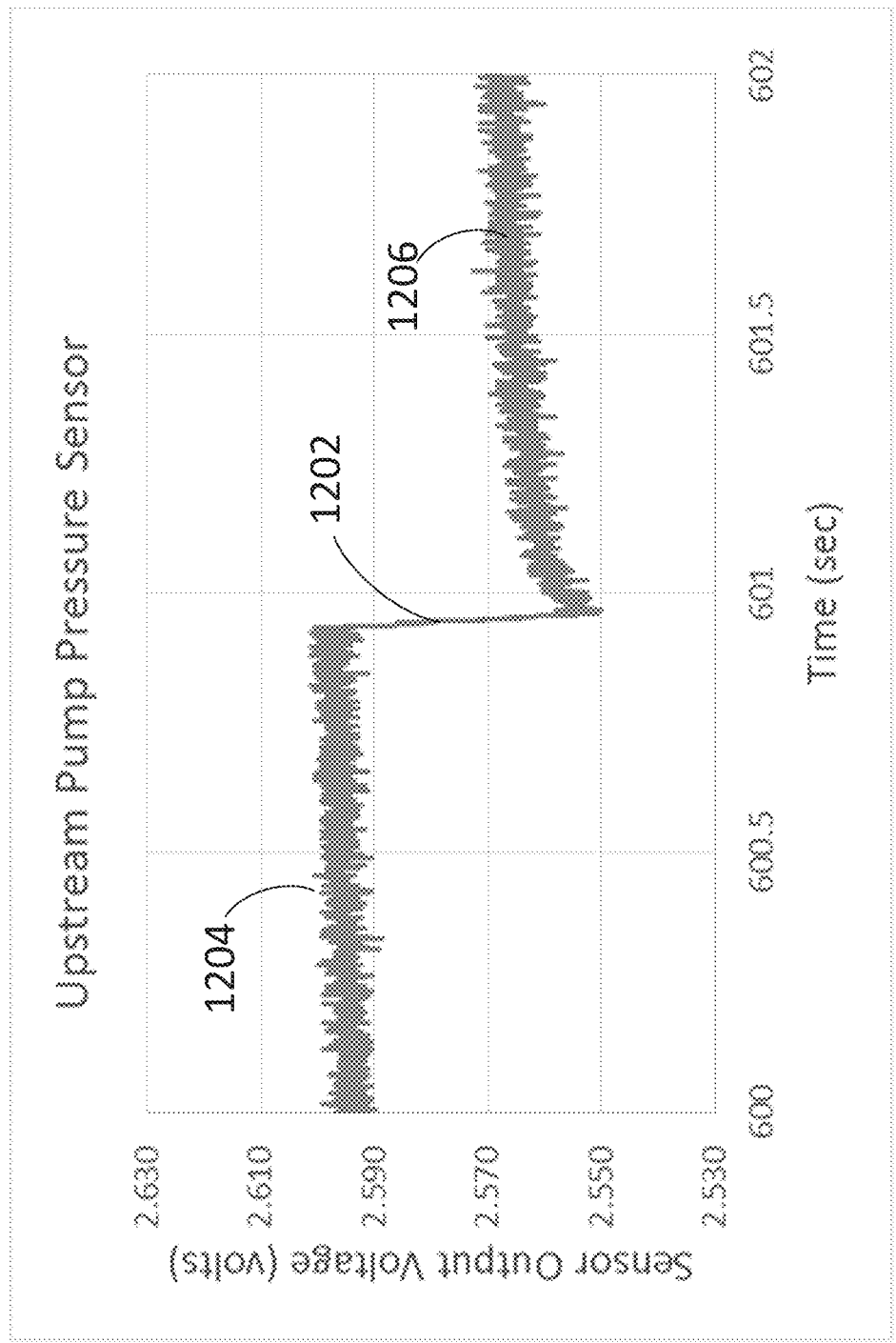
FIG. 12 shows an output of the upstream pump pressure sensor in the LVP pump for the flow rate profile shown in FIG. 8 under an upstream occlusion condition.

FIGS. 11 and 12 show the corresponding measured upstream pump pressure profiles from an upstream pump pressure sensor for a system operating under the flow rate profile shown in FIG. 8, according to various aspects of the subject technology. FIG. 11 shows the measurement recorded by the upstream pressure sensor when the system is operating normally. FIG. 12 shows the measurements recorded by the upstream pressure sensor when the system experiences an upstream occlusion.

FIG. 11 shows a first measured pressure spike 1102 that corresponds to the flow burst 802 shown in FIG. 8, and a second measured pressure spike 1104 corresponds to the flow burst 804 shown in FIG. 8. The measured pressure spikes 1102 and 1104 are measured in volts, from a voltage output of the downstream pressure sensor. The two measured pressure spikes are separated by a time interval 1106 that matches the time interval 806.

As shown in FIG. 9 and FIG. 10A, the value of a first (downstream) pressure 910 before the flow burst 802 is about the same as the value of a second (downstream) pressure 912 after the burst 802. In contrast, under downstream occlusion condition shown in FIG. 10B, a value of a fourth (downstream) pressure 1006 after the flow burst 802 is shifted upwards (e.g., by about 10-15 mV) compared with a value of a third (downstream) pressure 1004 before the flow burst 802.

FIG. 12 shows values of pressure measurements recorded under an upstream occlusion condition. A value of a second (upstream) pressure 1206 after the flow burst 802 is shifted downwards (e.g., by about 30 mV) compared with a value of a first (upstream) pressure 1204 before the flow burst.

In some implementations, measured pressure values are averaged (e.g., using an averaging function) over a selected duration (e.g., a few hundred milliseconds (ms), about 700 ms, about 600 ms, about 500 ms, about 400 ms, about 300 ms, about 200 ms, about 100 ms).

The second (downstream) pressure 912, the fourth (downstream) pressure 1006, and the second (upstream) pressure 1206, are all examples of $P_{after}$, a fluidic pressure after a flow burst. The first (downstream) pressure 910, the third (downstream) pressure 1004, and the first (upstream) pressure 1204 are examples of $P_{before}$, a fluidic pressure before a flow burst.

$\Delta P$ is the difference between $P_{after}$ and $P_{before}$ (e.g., $P_{after}-P_{before}$), or the pressure differential. A suitable threshold is selected for $\Delta P$ to determine if measured pressure values correspond to an occlusion condition. If the measured $\Delta P$ ($P_{after}-P_{before}$) exceeds the threshold, then a decision can be made annunciate an occlusion alarm.

A downstream occlusion condition exists when a measured pressure difference $\Delta P$ (i.e., $P_{after}-P_{before}$) is larger than a set downstream threshold (e.g., $Threshold_{downstream}$). An upstream occlusion condition exists when a measured pressure difference $\Delta P$ (i.e., $P_{after}-P_{before}$) is smaller than a set upstream threshold (e.g., $Threshold_{upstream}$). A magnitude of the measured pressure difference is always positive. An upstream occlusion condition also exists when a magnitude of the measured pressure difference $\Delta P$ (i.e., $P_{after}-P_{before}$) is greater than a set upstream threshold (e.g., $Threshold_{upstream}$).

In some implementations, a low pass filter is used to further improve a signal-to-noise in the pressure measurements from the upstream and/or downstream sensors. In some implementations, the low pass filter is for signals between less than 40 Hz so that noise from higher repetition rate sources (e.g., a pump motor operating a 1 kHz or random electrical noise) would be reduced (e.g., eliminated).

In some implementations, a band pass filter is used to further improve a signal-to-noise in the pressure measurements from the upstream and/or downstream sensors. In some implementations, the band pass filter is for signals between 1 Hz to 40 Hz so that noise from higher repetition rate sources (e.g., a pump motor operating a 1 kHz or random electrical noise) would be reduced (e.g., eliminated).

Figure 13:
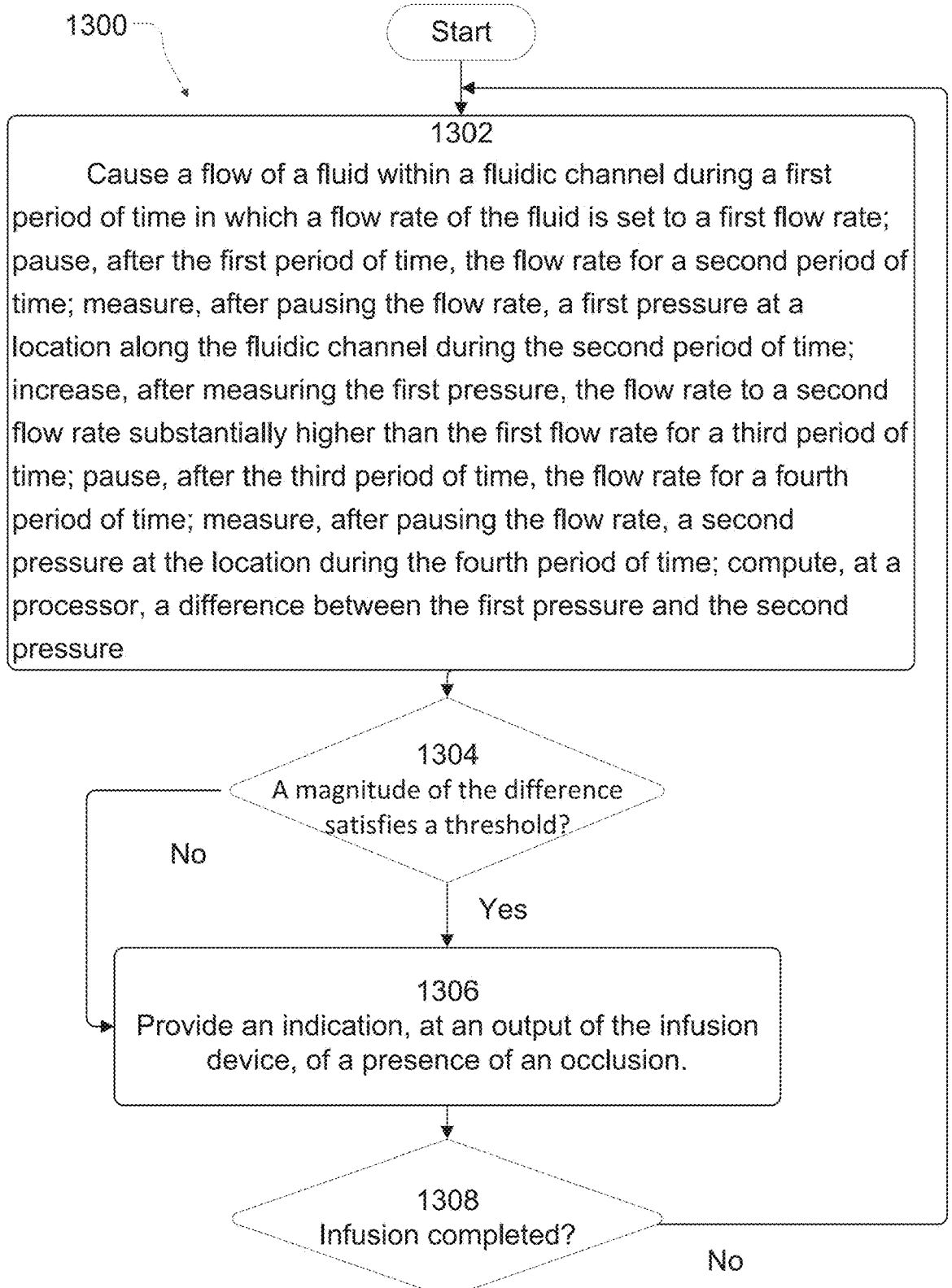
FIG. 13 depicts an example method for detecting an occlusion, according to aspects of the subject technology.

FIG. 13 depicts an example method for detecting an occlusion, according to aspects of the subject technology. For explanatory purposes, the various blocks of example method 1300 are described herein with reference to FIGS. 1-12, and the components and/or methods described herein. The one or more of the blocks of method 1300 may be implemented, for example, by one or more computing devices including, for example, medical device 12. In some implementations, one or more of the blocks may be implemented apart from other blocks, and by one or more different processors or devices. Further for explanatory purposes, the blocks of example method 1300 are described as occurring in serial, or linearly. However, multiple blocks of example method 1300 may occur in parallel. In addition, the blocks of example method 1300 need not be performed in the order shown and/or one or more of the blocks of example method 1300 need not be performed.

In the depicted example, the infusion device causes a flow of a fluid within a fluidic channel of the infusion device during a first period of time in which a flow rate of the fluid is set to a first flow rate. The infusion device pauses, after the first period of time, the flow rate for a second period of time; and measures, after pausing the flow rate, a first pressure at a location along the fluidic channel during the second period of time. The infusion device increases, after measuring the first pressure, the flow rate to a second flow rate substantially higher than the first flow rate for a third period of time; and pauses, after the third period of time, the flow rate for a fourth period of time. The infusion device measures, after pausing the flow rate, a second pressure at the location during the fourth period of time; and computes, at a processor, a difference between the first and second pressures (1302).

The processor determines whether the difference satisfies a threshold (1304).

Responsive to the value satisfying the threshold, an output of the infusion device provides an indication of a presence of an occlusion (1306). The indication may be a human perceivable indication such as via a user interface, light, sound, or haptic feedback. Also, the infusion device may transmit an alarm message (indication occlusion) via the server to a remote receiver such as nursing station in a hospital. In some implementations, the infusion device may additionally or alternatively adjust the operation of one or more physical elements included therein. For example, the infusion device may disable power to the motor driving the pump, initiate a back-off (e.g., reverse the syringe pump drive head to pull the plunger back), or the like to prevent additional pressure increases. The display of the infusion device may additionally or alternatively be adjusted. The infusion device may adjust operation of a second infusion device (e.g., infusion module). For example, if two modules are pumping different fluids to a patient, if one line is occluded, it may be desirable to adjust (or prevent) administration of the second fluid via the second infusion device.

The example method 1300 repeats steps 1302-1306 until infusion is completed (1308).

FIG. 14 is a conceptual diagram illustrating an example electronic system 1400 for automatically adapting control of a medical device responsive to detecting a hostile environment, according to aspects of the subject technology. Electronic system 1400 may be a computing device for execution of software associated with one or more portions or steps of method 1400, or components and methods provided by FIGS. 1-13, including but not limited to information system server 30, production server 204, computing hardware within patient care device 12, or terminal device 37. Electronic system 1400 may be representative, in combination with the disclosure regarding FIGS. 1-13. In this regard, electronic system 1400 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 1400 may include various types of computer readable media and interfaces for various other types of computer readable media. In the depicted example, electronic system 1400 includes a bus 1408, processing unit(s) 1412, a system memory 1404, a read-only memory (ROM) 1410, a permanent storage device 1402, an input device interface 1414, an output device interface 1406, and one or more network interfaces 1416. In some implementations, electronic system 1400 may include or be integrated with other computing devices or circuitry for operation of the various components and methods previously described.

Bus 1408 collectively represents all system, peripheral, and chipset buses that communicatively connect the numerous internal devices of electronic system 1400. For instance, bus 408 communicatively connects processing unit(s) 1412 with ROM 1410, system memory 1404, and permanent storage device 1402.

From these various memory units, processing unit(s) 1412 retrieves instructions to execute and data to process in order to execute the processes of the subject disclosure. The processing unit(s) can be a single processor or a multi-core processor in different implementations.

ROM 1410 stores static data and instructions that are needed by processing unit(s) 1412 and other modules of the electronic system. Permanent storage device 1402, on the other hand, is a read-and-write memory device. This device is a non-volatile memory unit that stores instructions and data even when electronic system 1400 is off. Some implementations of the subject disclosure use a mass-storage device (such as a magnetic or optical disk and its corresponding disk drive) as permanent storage device 402.

Other implementations use a removable storage device (such as a floppy disk, flash drive, and its corresponding disk drive) as permanent storage device 1402. Like permanent storage device 1402, system memory 1404 is a read-and-write memory device. However, unlike storage device 1402, system memory 1404 is a volatile read-and-write memory, such a random access memory. System memory 1404 stores some of the instructions and data that the processor needs at runtime. In some implementations, the processes of the subject disclosure are stored in system memory 1404, permanent storage device 1402, and/or ROM 1410. From these various memory units, processing unit(s) 1412 retrieves instructions to execute and data to process in order to execute the processes of some implementations.

Bus 1408 also connects to input and output device interfaces 1414 and 1406. Input device interface 1414 enables the user to communicate information and select commands to the electronic system. Input devices used with input device interface 1414 include, e.g., alphanumeric keyboards and pointing devices (also called "cursor control devices"). Output device interfaces 1406 enables, e.g., the display of images generated by the electronic system 1400. Output devices used with output device interface 1406 include, e.g., printers and display devices, such as cathode ray tubes (CRT) or liquid crystal displays (LCD). Some implementations include devices such as a touchscreen that functions as both input and output devices.

Also, as shown in FIG. 14, bus 1408 also couples electronic system 1400 to a network (not shown) through network interfaces 1416. Network interfaces 1416 may include, e.g., a wireless access point (e.g., Bluetooth or WiFi) or radio circuitry for connecting to a wireless access point. Network interfaces 1416 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 1400 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™ .NET™, C, C++, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, JSON, a custom protocol, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any implementation, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network).

"Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

In one aspect, a method for detecting an occlusion in a fluidic channel of an infusion device includes computing, at a processor, a difference between a first pressure at a location along the fluidic channel during a first time interval and a second pressure at the location during a second time interval later than the first time interval. The method includes determining whether a magnitude of the difference satisfies a threshold; and in accordance with a determination that the magnitude of the difference satisfies the threshold: providing an indication, at an output of the infusion device, of a presence of the occlusion. The first time interval is separated from the second time interval by a third time interval, a first flow rate during the first time interval and a second flow rate during the second time interval are both lower than a third flow rate during the third time interval.

In one aspect, a method for detecting an occlusion in a fluidic channel of an infusion device, includes flowing a fluid within the fluidic channel during a first period of time in which a flow rate of the fluid is set to a first flow rate; pausing, after the first period of time, the flow rate for a second period of time; measuring, after pausing the flow rate, a first pressure at a location along the fluidic channel during the second period of time; increasing, after measuring the first pressure, the flow rate to a second flow rate substantially higher than the first flow rate for a third period of time; pausing, after the third period of time, the flow rate for a fourth period of time; measuring, after pausing the flow rate, a second pressure at the location during the fourth period of time; computing, at a processor, a difference between the first and second pressures; determining whether a magnitude of the difference between the first and second pressures satisfies a threshold; and in accordance with a determination that the magnitude of the difference satisfies the threshold, providing an indication, at an output of the infusion device, of a presence of the occlusion.

In some implementations, the method includes receiving a selection to change an occlusion detection mode; and based on receiving the selection: pausing, after receiving the selection to change the occlusion detection mode, the flow rate for a fifth period of time; measuring a third pressure at a beginning portion of the fifth period of time; measuring a fourth pressure at an end portion of the fifth period of time; and computing, at the processor, a second difference between the third pressure and the fourth pressure; determining whether a magnitude of the second difference satisfies a second threshold; and in accordance with a determination that the magnitude of the second difference satisfies the second threshold, providing an indication, at the output of the infusion device, of a presence of the occlusion.

In some implementations, the method further includes stopping an infusion of the fluid, and sounding an alarm that indicates an occlusion condition when the magnitude of the second difference is equal to or smaller than the second threshold.

In some implementations, the method further includes continuing an infusion of the fluid, when the magnitude of the second difference is larger than the second threshold.

In some implementations, a fluid is infused along the fluidic channel at a preset flow rate, and the preset flow rate is driven by an infusion pump operating in burst mode. In some implementations, a fluid is infused along the fluidic channel at a preset flow rate, and a product of the preset flow rate with a first sum of the first time interval, second time interval, and the third time interval is equal to a second sum of (i) a product of the first flow rate with the first time interval, (ii) a product of the second flow rate with the second time interval, and (iii) a product of the third flow rate with the third time interval.

In some implementations, a fluid is infused along the fluidic channel at a preset flow rate, and the preset flow rate is driven by an infusion pump operating in burst mode. In some implementations, the third flow rate corresponds to a flow rate of an active period of the burst mode; and the first flow rate and the second flow rate correspond to a flow rate of an inactive period of the burst mode. In some implementations, the first flow rate and the second flow rate are zero.

In some implementations, the method further includes stopping an infusion of the fluid, and sounding an alarm that indicates a downstream occlusion condition when the first pressure is smaller than the second pressure, and the difference satisfies than the threshold.

In some implementations, the method further includes stopping an infusion of the fluid, and sounding an alarm that indicates an upstream occlusion condition when the first pressure is larger than the second pressure, and the difference satisfies the threshold.

In some implementations, computing the difference between the first pressure and the second pressure includes computing the difference in accordance with a determination that a downstream pressure sensor detects a rising slope of fluidic pressure of the fluid in the fluidic channel.

In some implementations, computing the difference between the first pressure and the second pressure includes computing the difference in accordance with a determination that an upstream pressure sensor detects a falling slope of fluidic pressure of the fluid in the fluidic channel.

In some implementations, a product of the second flow rate and the third period of time is a few microliters. In some implementations, the occlusion includes a downstream occlusion when the first pressure is smaller than the second pressure, and the magnitude of the difference satisfies the threshold. In some implementations, the occlusion includes an upstream occlusion when the first pressure satisfies the second pressure, and the magnitude of the difference satisfies the threshold.

In some implementations, the method further includes averaging over a first duration within the second period of time to obtain the first pressure; and averaging over a second duration within the fourth period of time to obtain the second pressure. In some implementations, the first duration is a few hundred milliseconds. In some implementations, the method further includes obtaining an averaged difference by computing additional pressure differences at the location at different time intervals, and providing the indication of the presence of the occlusion when a magnitude of the averaged difference satisfies the threshold.

In some implementations, providing an indication of a presence of an occlusion includes providing the indication at the output of the infusion device after repeating the computing and the determining for a set number of times. In some implementations, providing an indication of a presence of an occlusion includes incrementing a value of a counter each time the determination is made that the magnitude of the difference satisfies the threshold, and providing the indication of the presence when the value of the counter is equal to the set number of times. In some implementations, the method further includes adjusting a duration of the third period of time and a value of the second flow rate. In some implementations, a flow rate profile is formed by the first flow rate, the second flow rate and the third flow rate, and the infusion device generates the flow rate profile to detect the occlusion. In some implementations, providing the indication at the output of the infusion device includes presenting (e.g., sounding or adjusting a visual display) an alarm at the infusion device. In some implementations, providing the indication at the output of the infusion device includes showing a warning message on a display screen of the infusion device. In some implementations, the processor is a processor of the infusion device. In some implementations, the processor is a processor of a server to which the infusion device electronically communicates.

In some implementations, the threshold is adaptively adjusted based at least in part on a parameter of the infusion device. In some implementations, the threshold is adaptively adjusted between the first pressure and the second pressure. In some implementations, the method further includes using machine learning to determine the threshold. In some implementations, machine learning includes using training data sets of values of threshold associated with known occlusion conditions.

In one aspect, an infusion system includes an infusion device; and a processor configured to: control the infusion device to cause a fluid to flow within a fluidic channel of the infusion fluidic during a first period of time in which a flow rate of the fluidic is set to a first flow rate; control the infusion device to pause, after the first period of time, the flow rate for a second period of time, receive measurements, after pausing the flow rate, of a first pressure at a location along the fluidic channel during the second period of time; control the infusion device to increase, after measuring the first pressure, the flow rate to a second flow rate substantially higher than the first flow rate for a third period of time; control the infusion device to pause, after the third period of time, the flow rate for a fourth period of time; receive measurements, after pausing the flow rate, of a second pressure at the location during the fourth period of time; compute, a difference between the first and second pressures; determine whether a magnitude of the difference between the first and second pressures satisfies a threshold; and in accordance with determining that the magnitude of the difference satisfies the threshold: present, at an output of the infusion device, an indication of a presence of the occlusion.

What is claimed is:

1. A method for detecting an occlusion in a fluidic channel of an infusion device, comprising:
   causing, by the infusion device, a flow of a fluid within the fluidic channel during a first period of time in which a flow rate of the fluid is set to a first flow rate to cause the infusion device to administer the fluid to a patient;
   pausing, by the infusion device, after the first period of time, the flow of the fluid for a second period of time;
   measuring, after pausing the flow for the second period of time and while the flow is paused, a first pressure at a location along the fluidic channel during the second period of time;
   increasing, by the infusion device, after measuring the first pressure, the flow rate of the fluid from the paused flow to a second flow rate higher than the first flow rate for a third period of time;
   pausing, by the infusion device, after the third period of time, the flow of the fluid for a fourth period of time;
   measuring, after pausing the flow for the fourth period of time and while the flow is paused, a second pressure at the location during the fourth period of time;
   automatically controlling the infusion device to decrease, after measuring the second pressure, the flow of the fluid from the paused flow to a flow rate lower than the second flow rate, without user intervention;
   computing, at a processor, a difference between the first and second pressures;
   determining whether a magnitude of the difference between the first and second pressures satisfies a threshold; and
   in accordance with a determination that the magnitude of the difference satisfies the threshold, providing an indication, at an output of the infusion device, of a presence of the occlusion.

2. The method of claim 1, further comprising:
   receiving a selection to change an occlusion detection mode; and
   based on receiving the selection:
      pausing, after receiving the selection to change the occlusion detection mode, the flow rate for a fifth period of time;
   measuring a third pressure at a beginning portion of the fifth period of time;
   measuring a fourth pressure at an end portion of the fifth period of time; and
      computing, at the processor, a second difference between the third pressure and the fourth pressure;
   determining whether a magnitude of the second difference satisfies a second threshold; and
   in accordance with a determination that the magnitude of the second difference satisfies the second threshold, providing an indication, at the output of the infusion device, of a presence of the occlusion.

3. The method of claim 2, further comprising stopping an infusion of the fluid, and presenting an alarm that indicates an occlusion condition when the magnitude of the second difference is equal to or smaller than the second threshold.

4. The method of claim 2, further comprising continuing an infusion of the fluid, when the magnitude of the second difference is larger than the second threshold.

5. The method of claim 1, wherein a fluid is infused along the fluidic channel at a preset flow rate, and the preset flow rate is driven by an infusion pump operating in burst mode.

6. The method of claim 1, further comprising stopping an infusion of the fluid, and presenting an alarm that indicates a downstream occlusion condition when the first pressure is smaller than the second pressure, and the magnitude of the difference is larger than the threshold.

7. The method of claim 1, further comprising stopping an infusion of the fluid, and presenting an alarm that indicates an upstream occlusion condition when the first pressure is larger than the second pressure, and the magnitude of the difference is larger than the threshold.

8. The method of claim 1, wherein computing the difference between the first pressure and the second pressure includes computing the difference in accordance with a determination that a downstream pressure sensor detects a rising slope of fluidic pressure of a fluid in the fluidic channel.

9. The method of claim 1, wherein computing the difference between the first pressure and the second pressure includes computing the difference in accordance with a determination that an upstream pressure sensor detects a falling slope of fluidic pressure of a fluid in the fluidic channel.

10. The method of claim 1, wherein a product of the second flow rate and the third period of time is a few microliters.

11. The method of claim 1, further comprising:
averaging over a first duration within the second period of time to obtain the first pressure; and averaging over a second duration within the fourth period of time to obtain the second pressure.

12. The method of claim 1, wherein further comprising obtaining an averaged difference by computing additional pressure differences at the location at different time intervals, and providing the indication of the presence of the occlusion when a magnitude of the averaged difference satisfies the threshold.

13. The method of claim 1, wherein providing an indication of a presence of an occlusion includes providing the indication at the output of the infusion device after repeating the computing and the determining for a set number of times.

14. The method of claim 1, wherein a flow rate profile is formed by the first flow rate, the second flow rate and a third flow rate, and the infusion device generates the flow rate profile to detect the occlusion.

15. The method of claim 1, wherein providing the indication at the output of the infusion device comprises sounding an alarm at the infusion device.

16. The method of claim 1, wherein providing the indication at the output of the infusion device comprises showing a warning message on a display screen of the infusion device.

17. The method of claim 1, wherein the threshold is adaptively adjusted based at least in part on a parameter of the infusion device.

18. The method of claim 1, further comprising using machine learning to determine the threshold.

19. A non-transitory machine-readable storage medium embodying instructions that, when executed by a machine, allow the machine to perform a method for detecting an occlusion in a fluidic channel of an infusion device, the method comprising:
causing, by the infusion device, a flow of a fluid within the fluidic channel during a first period of time in which a flow rate of the fluid is set to a first flow rate to cause the infusion device to administer the fluid to a patient;
pausing, by the infusion device, after the first period of time, the flow of the fluid for a second period of time;
measuring, after pausing the flow for the second period of time and while the flow is paused, a first pressure at a location along the fluidic channel during the second period of time;
increasing, by the infusion device, after measuring the first pressure, the flow rate of the fluid from the paused flow to a second flow rate higher than the first flow rate for a third period of time;
pausing, by the infusion device, after the third period of time, the flow rate of the fluid for a fourth period of time;
measuring, after pausing the flow rate for the fourth period of time and while the flow is paused, a second pressure during the fourth period of time;
automatically controlling the machine to decrease, after measuring the second pressure, the flow of the fluid from the paused flow to a flow rate lower than the second flow rate, without user intervention;
computing, at a processor, a difference between the first and second pressures;
determining whether a magnitude of the difference between the first and second pressures satisfies a threshold; and
in accordance with a determination that the magnitude of the difference satisfies the threshold, providing an indication, at an output of the infusion device, of a presence of the occlusion.

20. An infusion system comprising:
an infusion device; and
a processor configured to:
control the infusion device to cause a flow of a fluid within a fluidic channel of the infusion device during a first period of time in which a flow rate of the fluid is set to a first flow rate to cause the infusion device to administer the fluid to a patient;
control the infusion device to pause, after the first period of time, the flow of the fluid for a second period of time,
receive measurements, after pausing the flow for the second period of time and while the flow is paused, of a first pressure at a location along the fluidic channel during the second period of time;
control the infusion device to increase, after measuring the first pressure, the flow rate of the fluid from the paused flow to a second flow rate higher than the first flow rate for a third period of time;
control the infusion device to pause, after the third period of time, the flow rate of the fluid for a fourth period of time;
receive measurements, after pausing the flow rate for the fourth period of time and while the flow is paused, of a second pressure at the location during the fourth period of time;
automatically controlling the infusion device to decrease, after measuring the second pressure, the flow of the fluid from the paused flow to a flow rate lower than the second flow rate, without user intervention;
compute, a difference between the first and second pressures;
determine whether a magnitude of the difference between the first and second pressures satisfies a threshold; and
in accordance with determining that the magnitude of the difference satisfies the threshold:
present, at an output of the infusion device, an indication of a presence of an occlusion.

* * * * *